(12) United States Patent
Yamada et al.

(10) Patent No.: US 7,169,592 B2
(45) Date of Patent: Jan. 30, 2007

(54) PRODUCING OPTICALLY ACTIVE AMINO COMPOUNDS

(75) Inventors: Yukio Yamada, Kakogawa (JP); Akira Iwasaki, Akashi (JP); Noriyuki Kizaki, Takasago (JP); Keiji Matsumoto, Nishinomiya (JP); Yasuhiro Ikenaka, Kobe (JP); Masahiro Ogura, Ono (JP); Junzo Hasegawa, Akashi (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 10/112,706

(22) Filed: Apr. 2, 2002

(65) Prior Publication Data

US 2002/0192786 A1  Dec. 19, 2002

Related U.S. Application Data

(62) Division of application No. 09/403,493, filed as application No. PCT/JP98/01814 on Apr. 20, 1998, now abandoned.

(30) Foreign Application Priority Data

Apr. 23, 1997  (JP)  .................................. 9-121732

(51) Int. Cl.
*C12N 9/10* (2006.01)
*C12N 1/21* (2006.01)
*C12N 15/54* (2006.01)
*C12N 15/63* (2006.01)
*C12N 15/82* (2006.01)
*C12N 15/85* (2006.01)
*C07H 21/04* (2006.01)

(52) U.S. Cl. .................. 435/193; 536/23.2; 435/252.3; 435/320.1; 435/325; 435/410

(58) Field of Classification Search ................ 435/193, 435/252.3, 252.33, 325, 410, 320.1; 536/23.2
See application file for complete search history.

(56) References Cited

U.S. PATENT DOCUMENTS

| | | | |
|---|---|---|---|
| 4,950,606 A | 8/1990 | Stirling et al. | 435/280 |
| 5,360,724 A | 11/1994 | Matcham et al. | 435/128 |
| 5,480,786 A | 1/1996 | Kretzschmar et al. | 435/106 |
| 5,814,473 A * | 9/1998 | Warren et al. | 435/15 |
| 6,221,638 B1 | 4/2001 | Yamada et al. | 435/128 |

FOREIGN PATENT DOCUMENTS

| | | |
|---|---|---|
| EP | A20189938 | 8/1986 |
| JP | 61181392 | 8/1986 |
| JP | 63273486 A | 11/1988 |
| JP | 3103192 | 4/1991 |
| JP | 6165687 | 6/1994 |
| WO | 9105870 | 5/1991 |
| WO | 9715682 | 5/1997 |

OTHER PUBLICATIONS

Iwasaki et al. (2006) Appl. Microbiol. Biotechnol., vol. 69, pp. 499-505.*
Abstract only, JP A6-2205790, Sep. 10, 1987.
Abstract only, JP A1-285193, Nov. 16, 1989.
Abstract only, JP A3-210189, Sep. 13, 1991.
Nakamichi et al. *Applied Microbiology and Biotechnology*, 33, 637-639 (1990).

* cited by examiner

*Primary Examiner*—Elizabeth Slobodyansky
(74) *Attorney, Agent, or Firm*—Birch, Stewart, Kolasch & Birch, LLP

(57) ABSTRACT

To provide a method for preparing optically active compounds, which mainly contain (R)-amino compounds, by microbial enzymes efficiently and inexpensively; a polypeptide having stereoselective transaminase activity which can be suitably used for the above preparation method; and a DNA encoding the polypeptide. A method for preparing an optically active amino compound, characterized in stereoselectively transaminating by acting a transaminase on an amino group acceptor, a ketone compound in the presence of an amino group donor, a primary amine; a DNA comprising a nucleotide sequence encoding a polypeptide having stereoselective transaminase activity; and a polypeptide having stereoselective transaminase activity obtainable from a culture of a microorganism belonging to the genus Arthrobacter.

9 Claims, 3 Drawing Sheets

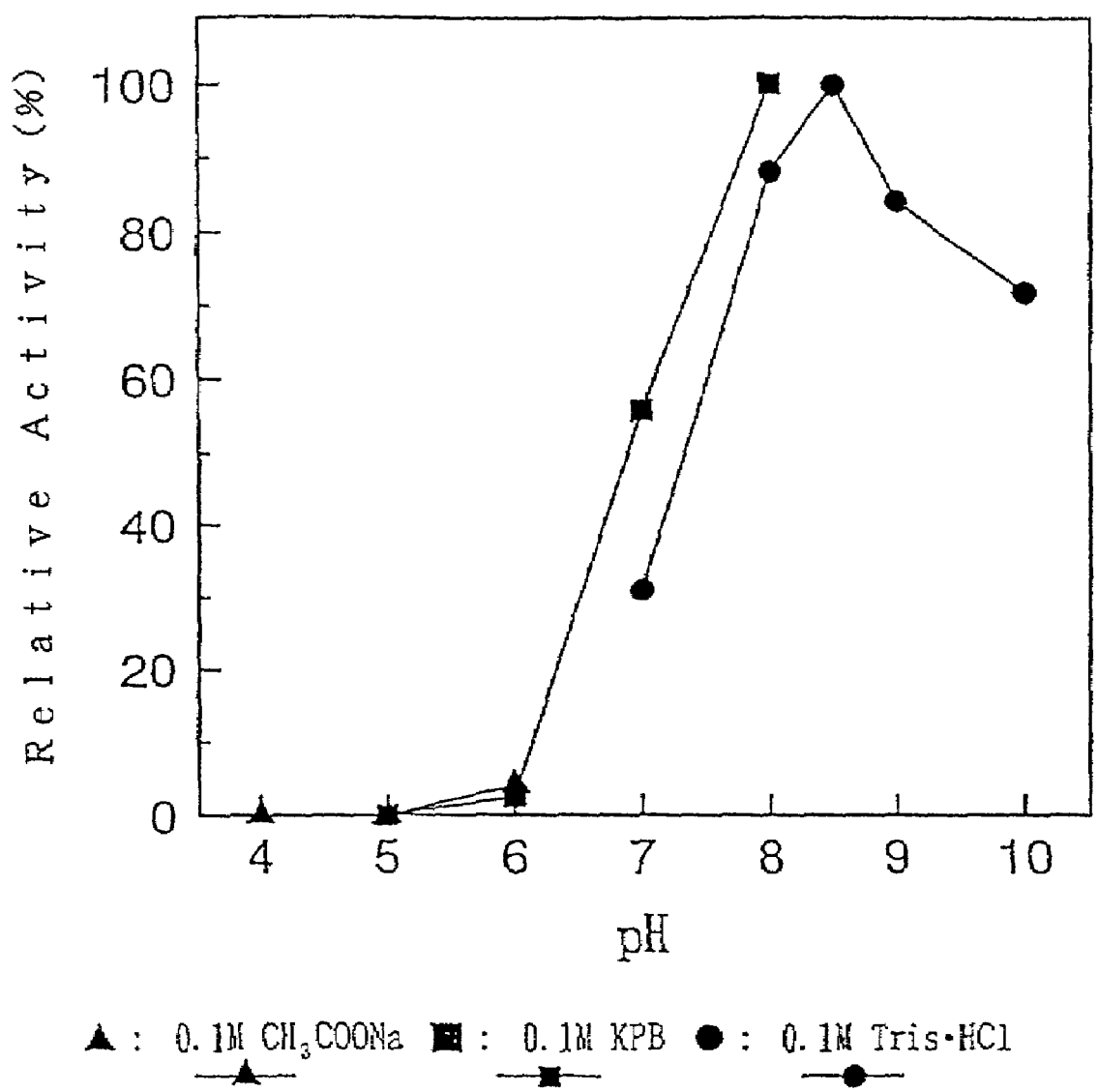
F I G. 1

SEQUENCE LISTING

<160> NUMBER OF SEQ ID NOS: 26

<210> SEQ ID NO 1
<211> LENGTH: 324
<212> TYPE: PRT
<213> ORGANISM: Arthrobacter sp.

<400> SEQUENCE: 1

```
Thr Ser Glu Ile Val Tyr Thr His Asp Thr Gly Leu Asp Tyr Ile Thr
1               5                   10                  15

Tyr Ser Asp Tyr Glu Leu Asp Pro Ala Asn Pro Leu Ala Gly Gly Ala
            20                  25                  30

Ala Trp Ile Glu Gly Ala Phe Val Pro Pro Ser Glu Ala Arg Ile Ser
        35                  40                  45

Ile Phe Asp Gln Gly Tyr Leu His Ser Asp Val Thr Tyr Thr Val Phe
    50                  55                  60

His Val Trp Asn Gly Asn Ala Phe Arg Leu Asp Asp His Ile Glu Arg
65                  70                  75                  80

Leu Phe Ser Asn Ala Glu Ser Met Arg Ile Ile Pro Pro Leu Thr Gln
                85                  90                  95

Asp Glu Val Lys Glu Ile Ala Leu Glu Leu Val Ala Lys Thr Glu Leu
            100                 105                 110

Arg Glu Ala Phe Val Ser Val Ser Ile Thr Arg Gly Tyr Ser Ser Thr
            115                 120                 125

Pro Gly Glu Arg Asp Ile Thr Lys His Arg Pro Gln Val Tyr Met Tyr
130                 135                 140

Ala Val Pro Tyr Gln Trp Ile Val Pro Phe Asp Arg Ile Arg Asp Gly
145                 150                 155                 160

Val His Ala Met Val Ala Gln Ser Val Arg Arg Thr Pro Arg Ser Ser
                165                 170                 175

Ile Asp Pro Gln Val Lys Asn Phe Gln Trp Gly Asp Leu Ile Arg Ala
            180                 185                 190

Val Gln Glu Thr His Asp Arg Gly Phe Glu Ala Pro Leu Leu Leu Asp
            195                 200                 205

Gly Asp Gly Leu Leu Ala Glu Gly Ser Gly Phe Asn Val Val Val Ile
210                 215                 220

Lys Asp Gly Val Val Arg Ser Pro Gly Arg Ala Ala Leu Pro Gly Ile
225                 230                 235                 240

Thr Arg Lys Thr Val Leu Glu Ile Ala Glu Ser Leu Gly His Glu Ala
                245                 250                 255

Ile Leu Ala Asp Ile Thr Leu Ala Glu Leu Leu Asp Ala Asp Glu Val
            260                 265                 270

Leu Gly Cys Thr Thr Ala Gly Gly Val Trp Pro Phe Val Ser Val Asp
        275                 280                 285

Gly Asn Pro Ile Ser Asp Gly Val Pro Gly Pro Ile Thr Gln Ser Ile
        290                 295                 300

Ile Arg Arg Tyr Trp Glu Leu Asn Val Glu Ser Ser Ser Leu Leu Thr
305                 310                 315                 320

Pro Val Gln Tyr
```

<210> SEQ ID NO 2
<211> LENGTH: 325
<212> TYPE: PRT
<213> ORGANISM: Arthrobacter sp.

<400> SEQUENCE: 2

```
Met Thr Ser Glu Ile Val Tyr Thr His Asp Thr Gly Leu Asp Tyr Ile
1               5                   10                  15

Thr Tyr Ser Asp Tyr Glu Leu Asp Pro Ala Asn Pro Leu Ala Gly Gly
            20                  25                  30

Ala Ala Trp Ile Glu Gly Ala Phe Val Pro Pro Ser Glu Ala Arg Ile
```

-continued

```
                  35                  40                  45
Ser Ile Phe Asp Gln Gly Tyr Leu His Ser Asp Val Thr Tyr Thr Val
 50                  55                  60

Phe His Val Trp Asn Gly Asn Ala Phe Arg Leu Asp Asp His Ile Glu
 65                  70                  75                  80

Arg Leu Phe Ser Asn Ala Glu Ser Met Arg Ile Ile Pro Pro Leu Thr
                     85                  90                  95

Gln Asp Glu Val Lys Glu Ile Ala Leu Glu Leu Val Ala Lys Thr Glu
                100                 105                 110

Leu Arg Glu Ala Phe Val Ser Val Ser Ile Thr Arg Gly Tyr Ser Ser
            115                 120                 125

Thr Pro Gly Glu Arg Asp Ile Thr Lys His Arg Pro Gln Val Tyr Met
130                 135                 140

Tyr Ala Val Pro Tyr Gln Trp Ile Val Pro Phe Asp Arg Ile Arg Asp
145                 150                 155                 160

Gly Val His Ala Met Val Ala Gln Ser Val Arg Arg Thr Pro Arg Ser
                165                 170                 175

Ser Ile Asp Pro Gln Val Lys Asn Phe Gln Trp Gly Asp Leu Ile Arg
            180                 185                 190

Ala Val Gln Glu Thr His Asp Arg Gly Phe Glu Ala Pro Leu Leu Leu
        195                 200                 205

Asp Gly Asp Gly Leu Leu Ala Glu Gly Ser Gly Phe Asn Val Val Val
210                 215                 220

Ile Lys Asp Gly Val Val Arg Ser Pro Gly Arg Ala Ala Leu Pro Gly
225                 230                 235                 240

Ile Thr Arg Lys Thr Val Leu Glu Ile Ala Glu Ser Leu Gly His Glu
                245                 250                 255

Ala Ile Leu Ala Asp Ile Thr Leu Ala Glu Leu Leu Asp Ala Asp Glu
            260                 265                 270

Val Leu Gly Cys Thr Thr Ala Gly Gly Val Trp Pro Phe Val Ser Val
        275                 280                 285

Asp Gly Asn Pro Ile Ser Asp Gly Val Pro Gly Pro Ile Thr Gln Ser
290                 295                 300

Ile Ile Arg Arg Tyr Trp Glu Leu Asn Val Glu Ser Ser Ser Leu Leu
305                 310                 315                 320

Thr Pro Val Gln Tyr
                325

<210> SEQ ID NO 3
<211> LENGTH: 329
<212> TYPE: PRT
<213> ORGANISM: Arthrobacter sp.

<400> SEQUENCE: 3

Ala Phe Ser Ala Asp Thr Ser Glu Ile Val Tyr Thr His Asp Thr Gly
 1               5                  10                  15

Leu Asp Tyr Ile Thr Tyr Ser Asp Tyr Glu Leu Asp Pro Ala Asn Pro
                20                  25                  30

Leu Ala Gly Gly Ala Ala Trp Ile Glu Gly Ala Phe Val Pro Pro Ser
             35                  40                  45

Glu Ala Arg Ile Ser Ile Phe Asp Gln Gly Tyr Leu His Ser Asp Val
        50                  55                  60

Thr Tyr Thr Val Phe His Val Trp Asn Gly Asn Ala Phe Arg Leu Asp
 65                  70                  75                  80
```

-continued

```
Asp His Ile Glu Arg Leu Phe Ser Asn Ala Glu Ser Met Arg Ile Ile
            85                  90                  95

Pro Pro Leu Thr Gln Asp Glu Val Lys Glu Ile Ala Leu Glu Leu Val
            100                 105                 110

Ala Lys Thr Glu Leu Arg Glu Ala Phe Val Ser Val Ser Ile Thr Arg
            115                 120                 125

Gly Tyr Ser Ser Thr Pro Gly Glu Arg Asp Ile Thr Lys His Arg Pro
130                 135                 140

Gln Val Tyr Met Tyr Ala Val Pro Tyr Gln Trp Ile Val Pro Phe Asp
145                 150                 155                 160

Arg Ile Arg Asp Gly Val His Ala Met Val Ala Gln Ser Val Arg Arg
                165                 170                 175

Thr Pro Arg Ser Ser Ile Asp Pro Gln Val Lys Asn Phe Gln Trp Gly
                180                 185                 190

Asp Leu Ile Arg Ala Val Gln Glu Thr His Asp Arg Gly Phe Glu Ala
            195                 200                 205

Pro Leu Leu Leu Asp Gly Asp Gly Leu Leu Ala Glu Gly Ser Gly Phe
210                 215                 220

Asn Val Val Val Ile Lys Asp Gly Val Val Arg Ser Pro Gly Arg Ala
225                 230                 235                 240

Ala Leu Pro Gly Ile Thr Arg Lys Thr Val Leu Glu Ile Ala Glu Ser
                245                 250                 255

Leu Gly His Glu Ala Ile Leu Ala Asp Ile Thr Leu Ala Glu Leu Leu
                260                 265                 270

Asp Ala Asp Glu Val Leu Gly Cys Thr Thr Ala Gly Gly Val Trp Pro
            275                 280                 285

Phe Val Ser Val Asp Gly Asn Pro Ile Ser Asp Gly Val Pro Gly Pro
290                 295                 300

Ile Thr Gln Ser Ile Ile Arg Arg Tyr Trp Glu Leu Asn Val Glu Ser
305                 310                 315                 320

Ser Ser Leu Leu Thr Pro Val Gln Tyr
                325

<210> SEQ ID NO 4
<211> LENGTH: 330
<212> TYPE: PRT
<213> ORGANISM: Arthrobacter sp.

<400> SEQUENCE: 4

Met Ala Phe Ser Ala Asp Thr Ser Glu Ile Val Tyr Thr His Asp Thr
1               5                   10                  15

Gly Leu Asp Tyr Ile Thr Tyr Ser Asp Tyr Glu Leu Asp Pro Ala Asn
            20                  25                  30

Pro Leu Ala Gly Gly Ala Ala Trp Ile Glu Gly Ala Phe Val Pro Pro
            35                  40                  45

Ser Glu Ala Arg Ile Ser Ile Phe Asp Gln Gly Tyr Leu His Ser Asp
            50                  55                  60

Val Thr Tyr Thr Val Phe His Val Trp Asn Gly Asn Ala Phe Arg Leu
65                  70                  75                  80

Asp Asp His Ile Glu Arg Leu Phe Ser Asn Ala Glu Ser Met Arg Ile
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Phe Val Ser Val Ser Ile Thr
            115                 120                 125
```

Arg Gly Tyr Ser Ser Thr Pro Gly Glu Arg Asp Ile Thr Lys His Arg
            130                 135                 140

Pro Gln Val Tyr Met Tyr Ala Val Pro Tyr Gln Trp Ile Val Pro Phe
145                 150                 155                 160

Asp Arg Ile Arg Asp Gly Val His Ala Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Val Gln Glu Thr His Asp Arg Gly Phe Glu
            195                 200                 205

Ala Pro Leu Leu Leu Asp Gly Asp Gly Leu Leu Ala Glu Gly Ser Gly
210                 215                 220

Phe Asn Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Leu Ala Glu Leu
            260                 265                 270

Leu Asp Ala Asp Glu Val Leu Gly Cys Thr Thr Ala Gly Gly Val Trp
            275                 280                 285

Pro Phe Val Ser Val Asp Gly Asn Pro Ile Ser Asp Gly Val Pro Gly
290                 295                 300

Pro Ile Thr Gln Ser Ile Ile Arg Arg Tyr Trp Glu Leu Asn Val Glu
305                 310                 315                 320

Ser Ser Ser Leu Leu Thr Pro Val Gln Tyr
                325                 330

<210> SEQ ID NO 5
<211> LENGTH: 978
<212> TYPE: DNA
<213> ORGANISM: Arthrobacter sp.

<400> SEQUENCE: 5
atgacctccg agatcgtcta cacgcacgac accggcctcg actacatcac ttatagcgac      60
tacgaactcg atcctgctaa cccgctcgcg ggaggtgcgg catggatcga gggtgcattc     120
gtgccgccgt cggaggcgcg gatctcgatc ttcgatcagg gttacctcca ctcggacgtc     180
acctacacgg tcttccacgt ctggaacgga atgcattcc gcctcgacga ccacatcgaa      240
cgcctcttct ccaacgcgga gtcgatgcgc atcatccctc cgctcacaca ggacgaagtg     300
aaggagattg cgctcgaact cgtcgcgaag accgaattgc gtgaggcctt cgtgtccgtg     360
tcgattaccc gcggttacag ctcgactccg ggcgagcgcg acatcacgaa gcaccgcccg     420
caggtgtaca tgtatgccgt cccatatcag tggatcgtgc cgtttgaccg aattcgcgac     480
ggcgtgcacg ccatggtcgc acagagcgtg cgccgaaccc cgcgcagctc gatcgaccct     540
caggtcaaga acttccagtg ggggatctg atccgtgcgg ttcaagagac gcacgaccgc      600
gggttcgagg ctccccttct gctcgacggc gatggactgc ttgccgaggg ctcgggttc      660 aacgtcgtcg tgatcaagga cggcgtcgtg cgcagcccgg gtcgagcggc gctccccggc    720
attacgcgga agaccgtgct cgagatcgcc gaatcgctcg gacacgaggc gattctcgcc   780
gacatcacgc tcgctgaact gctcgacgcc gacgaagtgc tcggctgcac gactgcgggc    840
ggagtgtggc cattcgtcag cgtggacggg aaccccatct cggacggggt tcccggcccc   900
atcacccagt cgatcatccg tcgttactgg gagctgaatg tcgagagctc gtcgttgctt   960

```
acgcctgtgc agtactga                                              978

<210> SEQ ID NO 6
<211> LENGTH: 993
<212> TYPE: DNA
<213> ORGANISM: Arthrobacter sp.

<400> SEQUENCE: 6
gtggcattca gcgccgatac ctccgagatc gtctacacgc acgacaccgg cctcgactac    60
atcacttata gcgactacga actcgatcct gctaacccgc tcgcgggagg tgcggcatgg   120
atcgagggtg cattcgtgcc gccgtcggag gcgcggatct cgatcttcga tcagggttac   180
ctccactcgg acgtcaccta cacggtcttc cacgtctgga acggaaatgc attccgcctc   240
gacgaccaca tcgaacgcct cttctccaac gcggagtcga tgcgcatcat ccctccgctc   300
acacaggacg aagtgaagga gattgcgctc gaactcgtcg cgaagaccga attgcgtgag   360
gccttcgtgt ccgtgtcgat tacccgcggt tacagctcga ctccgggcga gcgcgacatc   420
acgaagcacc gcccgcaggt gtacatgtat gccgtcccat atcagtggat cgtgccgttt   480
gaccgaattc gcgacggcgt gcacgccatg gtcgcacaga gcgtgcgccg aaccccgcgc   540
agctcgatcg accctcaggt caagaacttc cagtgggggg atctgatccg tgcggttcaa   600
gagacgcacg accgcgggtt cgaggctccc cttctgctcg acggcgatgg actgcttgcc   660
gagggctcgg ggttcaacgt cgtcgtgatc aaggacggcg tcgtgcgcag cccgggtcga   720
gcggcgctcc ccggcattac gcggaagacc gtgctcgaga tcgccgaatc gctcggacac   780
gaggcgattc tcgccgacat cacgctcgct gaactgctcg acgccgacga agtgctcggc   840
tgcacgactg cgggcggagt gtggccattc gtcagcgtgg acggcaaccc catctcggac   900
ggggttcccg gccccatcac ccagtcgatc atccgtcgtt actgggagct gaatgtcgag   960
agctcgtcgt tgcttacgcc tgtgcagtac tga                               993

<210> SEQ ID NO 7
<211> LENGTH: 993
<212> TYPE: DNA
<213> ORGANISM: Arthrobacter sp.

<400> SEQUENCE: 7
atggcattca gcgccgatac ctccgagatc gtctacacgc acgacaccgg cctcgactac    60
atcacttata gcgactacga actcgatcct gctaacccgc tcgcgggagg tgcggcatgg   120
atcgagggtg cattcgtgcc gccgtcggag gcgcggatct cgatcttcga tcagggttac   180
ctccactcgg acgtcaccta cacggtcttc cacgtctgga acggaaatgc attccgcctc   240
gacgaccaca tcgaacgcct cttctccaac gcggagtcga tgcgcatcat ccctccgctc   300
acacaggacg aagtgaagga gattgcgctc gaactcgtcg cgaagaccga attgcgtgag   360
gccttcgtgt ccgtgtcgat tacccgcggt tacagctcga ctccgggcga gcgcgacatc   420
acgaagcacc gcccgcaggt gtacatgtat gccgtcccat atcagtggat cgtgccgttt   480
gaccgaattc gcgacggcgt gcacgccatg gtcgcacaga gcgtgcgccg aaccccgcgc   540
agctcgatcg accctcaggt caagaacttc cagtgggggg atctgatccg tgcggttcaa   600
gagacgcacg accgcgggtt cgaggctccc cttctgctcg acggcgatgg actgcttgcc   660
gagggctcgg ggttcaacgt cgtcgtgatc aaggacggcg tcgtgcgcag cccgggtcga   720
gcggcgctcc ccggcattac gcggaagacc gtgctcgaga tcgccgaatc gctcggacac   780
```

```
gaggcgattc tcgccgacat cacgctcgct gaactgctcg acgccgacga agtgctcggc      840
tgcacgactg cgggcggagt gtggccattc gtcagcgtgg acggcaaccc catctcggac      900
ggggttcccg gccccatcac ccagtcgatc atccgtcgtt actgggagct gaatgtcgag      960
agctcgtcgt tgcttacgcc tgtgcagtac tga                                   993
```

<210> SEQ ID NO 8
<211> LENGTH: 19
<212> TYPE: PRT
<213> ORGANISM: Arthrobacter sp.
<220> FEATURE:
<221> NAME/KEY: UNSURE
<222> LOCATION: (1)..(1)
<223> OTHER INFORMATION: Xaa = any amino acid
<221> NAME/KEY: UNSURE
<222> LOCATION: (2)..(2)
<223> OTHER INFORMATION: Xaa = any amino acid
<221> NAME/KEY: UNSURE
<222> LOCATION: (15)..(15)
<223> OTHER INFORMATION: Xaa = any amino acid

<400> SEQUENCE: 8

```
Xaa Xaa Ser Ala Asp Thr Ser Glu Ile Val Tyr Thr His Asp Xaa Gly
1               5                   10                  15

Leu Asp Tyr
```

<210> SEQ ID NO 9
<211> LENGTH: 20
<212> TYPE: PRT
<213> ORGANISM: Arthrobacter sp.

<400> SEQUENCE: 9

```
Thr Ser Glu Ile Val Tyr Thr His Asp Thr Gly Leu Asp Tyr Ile Thr
1               5                   10                  15

Tyr Ser Asp Tyr
            20
```

<210> SEQ ID NO 10
<211> LENGTH: 11
<212> TYPE: PRT
<213> ORGANISM: Arthrobacter sp.

<400> SEQUENCE: 10

```
Ala Val Pro Tyr Gln Trp Lys Val Pro Phe Asp
1               5                   10
```

<210> SEQ ID NO 11
<211> LENGTH: 18
<212> TYPE: PRT
<213> ORGANISM: Arthrobacter sp.

<400> SEQUENCE: 11

```
Ile Ser Ile Phe Asp Gln Gly Tyr Leu His Ser Asp Val Thr Tyr Thr
1               5                   10                  15

Val Phe
```

<210> SEQ ID NO 12
<211> LENGTH: 29
<212> TYPE: DNA
<213> ORGANISM: Artificial Sequence
<220> FEATURE:
<223> OTHER INFORMATION: Oligonucleotide was synthesized based on the
      amino acid sequences of SEQ ID NOS:8, 9 and 10 which amino acid
      sequences originated from Arthrobacter sp.
<221> NAME/KEY: misc_feature -continued

```
<222> LOCATION: (18)..(18)
<223> OTHER INFORMATION: n = a, t, c, or g
<221> NAME/KEY: misc_feature
<222> LOCATION: (24)..(24)
<223> OTHER INFORMATION: n = a, t, c, or g

<400> SEQUENCE: 12
cgcggatccg arathgtnta yacncayga                                    29

<210> SEQ ID NO 13
<211> LENGTH: 17
<212> TYPE: DNA
<213> ORGANISM: Artificial Sequence
<220> FEATURE:
<223> OTHER INFORMATION: Oligonucleotide was synthesized based on the
      amino acid sequences of SEQ ID NOS:8, 9 and 10 which amino acid
      sequences originated from Arthrobacter sp.
<221> NAME/KEY: misc_feature
<222> LOCATION: (15)..(15)
<223> OTHER INFORMATION: n = a, c, t, or g

<400> SEQUENCE: 13
acyttccayt grtangg                                                 17

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide was synthesized based on the
      nucleotide sequences illucidated using primers derived from the
      amino acid sequences of SEQ ID NOS:8, 9 and 10 which amino acid
      sequences originated from Arthrobacter sp.

<400> SEQUENCE: 14
gcatcatccc tccgctcaca                                              20

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide was synthesized based on the
      nucleotide sequences illucidated using primers derived from the
      amino acid sequences of SEQ ID NOS:8, 9 and 10 which amino acid
      sequences originated from Arthrobacter sp.

<400> SEQUENCE: 15
gaactcgatc ctgctaaccc                                              20

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide was synthesized based on the
      nucleotide sequences illucidated using primers derived from the
      amino acid sequences of SEQ ID NOS:8, 9 and 10 which amino acid
      sequences originated from Arthrobacter sp.

<400> SEQUENCE: 16
tgtgagcgga gggatgatgc                                              20

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide was synthesized based on the
```

```
            nucleotide sequences illucidated using primers derived from the
            amino acid sequences of SEQ ID NOS:8, 9 and 10 which amino acid
            sequences originated from Arthrobacter sp.

<400> SEQUENCE: 17
gcggagtgtg gccattcgtc                                                     20

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide was synthesized based on the
            nucleotide sequences illucidated using primers derived from the
            amino acid sequences of SEQ ID NOS:8, 9 and 10 which amino acid
            sequences originated from Arthrobacter sp.

<400> SEQUENCE: 18
ggcacgaatg caccctcgat                                                     20

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide was synthesized based on the
            nucleotide sequences illucidated using primers derived from the
            amino acid sequences of SEQ ID NOS:8, 9 and 10 which amino acid
            sequences originated from Arthrobacter sp.

<400> SEQUENCE: 19
cgtagtcgct ataagtgatg                                                     20

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide was synthesized based on the
            nucleotide sequences illucidated using primers derived from the
            amino acid sequences of SEQ ID NOS:8, 9 and 10 which amino acid
            sequences originated from Arthrobacter sp.

<400> SEQUENCE: 20
ccttctacga cgacccgaag                                                     20

<210> SEQ ID NO 21
<211> LENGTH: 1574
<212> TYPE: DNA
<213> ORGANISM: Arthrobacter sp.

<400> SEQUENCE: 21
ctgcaggcgc cctacgagct cgtcctcgag gtcgccgaga ccggcaagct ccccgtcgtt         60
ctcttcacgg ccggtggcgt cgccaccccc gcggatgccg cgatgatgat gcagctcgga        120
gcagacggtg tcttcgtcgg ctcgggcatc ttcaagtcgg gcaatcccga ggagcgcgcc        180
gctgcgatcg tcaaggctgt ggccttctac gacgacccga aggtcatcgc tgaggtctcg        240
cgcggtctcg gagaggccat ggtcggcatc aacgtcggcg acctcccgc tccgcaccga        300 ctcgccgagc gcgggtggtg acgaccctcc acgagattcc tgtccgtgat tcccctcctc        360
cgaaccccat cagaaaggca ccaccgtggc attcagcgcc gataccctccg agatcgtcta        420 cacgcacgac accggcctcg actacatcac ttatagcgac tacgaactcg atcctgctaa        480
cccgctcgcg ggaggtgcgg catggatcga gggtgcattc gtgccgccgt cggaggcgcg        540
```

-continued

| | |
|---|---|
| gatctcgatc ttcgatcagg gttacctcca ctcggacgtc acctacacgg tcttccacgt | 600 |
| ctggaacgga aatgcattcc gcctcgacga ccacatcgaa cgcctcttct ccaacgcgga | 660 |
| gtcgatgcgc atcatccctc cgctcacaca ggacgaagtg aaggagattg cgctcgaact | 720 |
| cgtcgcgaag accgaattgc gtgaggcctt cgtgtccgtg tcgattaccc gcggttacag | 780 |
| ctcgactccg ggcgagcgcg acatcacgaa gcaccgcccg caggtgtaca tgtatgccgt | 840 |
| cccatatcag tggatcgtgc cgtttgaccg aattcgcgac ggcgtgcacg ccatggtcgc | 900 |
| acagagcgtg cgccgaaccc cgcgcagctc gatcgaccct caggtcaaga acttccagtg | 960 |
| gggggatctg atccgtgcgg ttcaagagac gcacgaccgc gggttcgagg ctccccttct | 1020 |
| gctcgacggc gatggactgc ttgccgaggg ctcggggttc aacgtcgtcg tgatcaagga | 1080 |
| cggcgtcgtg cgcagcccgg gtcgagcggc gctccccggc attacgcgga agaccgtgct | 1140 |
| cgagatcgcc gaatcgctcg gacacgaggc gattctcgcc gacatcacgc tcgctgaact | 1200 |
| gctcgacgcc gacgaagtgc tcggctgcac gactgcgggc ggagtgtggc cattcgtcag | 1260 |
| cgtggacggc aaccccatct cggacggggt tcccggcccc atcacccagt cgatcatccg | 1320 |
| tcgttactgg gagctgaatg tcgagagctc gtcgttgctt acgcctgtgc agtactgaat | 1380 |
| ccgatcagtg aggggtcgac atctctcgac ccctcacggc aactcccgag aggcaggatg | 1440 |
| tatgacagcc ggtcgaacga tcacgatcga cgccgatgcc atcacgcaca acgtcgcccg | 1500 |
| catcgtgcat gccaccgcgc cgagttcggt gatcgcggtg gtgaaggccg acggctacgg | 1560 |
| tcacggcgct gcag | 1574 |

<210> SEQ ID NO 22
<211> LENGTH: 30
<212> TYPE: DNA
<213> ORGANISM: Artificial Sequence
<220> FEATURE:
<223> OTHER INFORMATION: Amino terminal primer for introduction of
      restriction site in Escherichia coli expression vector.

<400> SEQUENCE: 22
acacatatgg cattcagcgc cgatacctcc                                30

<210> SEQ ID NO 23
<211> LENGTH: 30
<212> TYPE: DNA
<213> ORGANISM: Artificial Sequence
<220> FEATURE:
<223> OTHER INFORMATION: Amino terminal primer for introduction of
      restriction site in Escherichia coli expression vector.

<400> SEQUENCE: 23
acacatatga cctccgagat cgtctacacg                                30

<210> SEQ ID NO 24
<211> LENGTH: 30
<212> TYPE: DNA
<213> ORGANISM: Artificial Sequence
<220> FEATURE:
<223> OTHER INFORMATION: Amino terminal primer for introduction of
      restriction site in Escherichia coli expression vector.

<400> SEQUENCE: 24
agacacgtgg cattcagcgc cgatacctcc                                30

<210> SEQ ID NO 25
<211> LENGTH: 30
<212> TYPE: DNA

```
<213> ORGANISM: Artificial Sequence
<220> FEATURE:
<223> OTHER INFORMATION: Carboxyl terminal primer for introduction of
      restriction site in Escherichia coli expression vector.

<400> SEQUENCE: 25
agaggatcct cagtactgca caggcgtaag                                         30

<210> SEQ ID NO 26
<211> LENGTH: 465
<212> TYPE: DNA
<213> ORGANISM: Arthrobacter sp.

<400> SEQUENCE: 26
ggatccgaga ttgtctatac acacgacacc ggcctcgact acatcactta tagcgactac        60
gaactcgatc ctgctaaccc gctcgcggga ggtgcggcat ggatcgaggg tgcattcgtg       120
ccgccgtcgg aggcgcggat ctcgatcttc gatcagggtt acctccactc ggacgtcacc       180
tacacggtct tccacgtctg aacggaaat gcattccgcc tcgacgacca catcgaacgc        240
ctcttctcca acgcggagtc gatgcgcatc atccctccgc tcacacagga cgaagtgaag       300
gagattgcgc tcgaactcgt cgcgaagacc gaattgcgtg aggccttcgt gtccgtgtcg       360
attacccgcg gttacagctc gactccgggc gagcgcgaca tcacgaagca ccgcccgcag       420
gtgtacatgt atgccgtccc ataccagtgg aaagtaatcg gatcc                      465
```

PRODUCING OPTICALLY ACTIVE AMINO COMPOUNDS

This application is a 37 C.F.R. § 1.53(b) divisional of application Ser. No. 09/403,493, filed on Oct. 22, 1999, now abandoned the entire contents of which is hereby incorporated by reference, which is the national phase under 35 U.S.C. § 371 of PCT International Application No. PCT/JP98/01814, which has an International filing date of Apr. 20, 1998, which designated the United States of America.

TECHNICAL FIELD

The present invention relates to optically active amino compounds having an aryl group and the like at the 1-position, which can be used as intermediates for pharmaceuticals and agricultural chemicals. 1-(3,4-Dimethoxyphenyl)-2-aminopropane, which is one of the desired compounds of the present invention, is an important compound as intermediates for CL316G, 243 [J. D. Bloom et al., *J. Med. Chem.* 35, 3081–3084 (1992)] and analogous compounds thereof, which are promising as antidiabetics and agents for antiobesity under development.

In addition, (S)-2-amino-1-methoxypropane, which is another desired compound is a useful compound which can be used as intermediates for herbicides.

BACKGROUND ART

Processes for preparing optically active amino compounds having an aryl group and the like at the 1-position by using an enzyme include a report in Nakamichi et al. [*Appl. Microbiol. Biotechnol.*, 33, 634–640 (1990)] and Japanese Examined Patent Publication No. Hei 4-11194. It is disclosed in these publications that an (S)-form can be efficiently prepared by enzymatically transaminating to 1-(substituted phenyl)-2-propanones. Further, Japanese Examined Patent Publication No. Hei 4-11194 also discloses a synthesis of an (R)-form; however, the present inventors have conducted additional experiment to examine microorganisms and substrate disclosed in Japanese Examined Patent Publication No. Hei 4-11194 and found that the reproducibility by means of this method is very poor, and thereby making it difficult to use this method for practical purposes.

Further, Stirling et al. disclose a method in which only the (S)-form is decomposed by actions of an ω-amino acid transaminase to a racemic amino compound produced by an organic synthesis, to thereby obtain the remaining (R)-form (Japanese Patent Laid-Open No. Hei 3-103192). However, in this method, since the (S)-form is decomposed to obtain the (R)-form, the yield against the substrate is lowered to 50% or less, so that this method cannot be considered to be advantageous from the aspect of costs. In addition, Stirling et al., the authors as above, also disclose a method in which only (S)-amino compounds are prepared from a ketone-form by using an ω-amino acid transaminase in the presence of an amino donor. However, optically active (R)-amino compounds cannot be prepared by this method.

DISCLOSURE OF INVENTION

Accordingly, an object of the present invention is to provide a method for preparing optically active compounds, which mainly contain (R)-amino compounds, by microbial enzymes efficiently and inexpensively. A further object of the present invention is to provide a polypeptide having stereoselective transaminase activity which can be suitably used for the above preparation method, and a DNA encoding the polypeptide.

The present inventors have found a microorganism from soil, the microorganism being capable of synthesizing an optically active amino compound, such as (R)-1-(3,4-dimethoxyphenyl)-2-aminopropane, with good yield by transaminating in (R)-form selectivity to a ketone compound having an aryl group, and the like, including, for instance, 1-(3,4-dimethoxyphenyl)-2-propanone, at the 1-position. Further studies have been made on the reaction using the microorganism, and thereby the present inventors have found a microorganism from soil, the microorganism being capable of synthesizing various optically active amino compounds, wherein many of the resulting compounds have (R)-form as mentioned above, and there may be some having (S)-form as in the case, for instance, (S)-2-phenylglycinol, depending on its relationship with the substituent bound to asymmetric carbon. Further studies have been made on the reaction using the microorganism, and at the same time the present inventors have isolated a gene for enzyme participating in the reaction (hereinafter referred to as "transaminase"). Therefore, studies have been made on a method for preparing transaminase inexpensively comprising using a recombinant microorganism in which *Escherichia coli*, or the like is used as a host, and the present invention has been completed.

Specifically, the present invention, in essence, pertains to:

[1] a method for preparing an optically active amino compound, characterized in stereoselectively transaminating by acting a transaminase on an amino group acceptor, a ketone compound, represented by the following general formula (1):

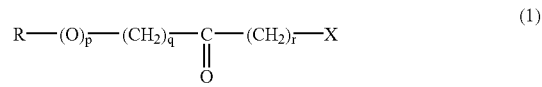

wherein p is 0 or 1; q is an integer of 0 to 8; r is an integer of 0 to 4; R is any one of a substituted or unsubstituted aryl group having 6 to 14 carbon atoms, a heteroaryl group having 4 to 12 carbon atoms, carboxyl group, an alkoxycarbonyl group having 1 to 6 carbon atoms, methyl group or hydrogen atom; and X is any one of hydroxyl group, carboxyl group, an alkoxycarbonyl group having 1 to 6 carbon atoms or hydrogen atom, in the presence of an amino group donor, a primary amine, to thereby give an optically active amino compound corresponding thereto;

[2] the method according to item [1] above, wherein the transamination is carried out (R)-form selectively, to give an optically active amino compound of (R)-form;

[3] the method according to item [1] or [2] above, wherein the substituted aryl group is an aryl group substituted at one or more sites by one or more substituents selected from the group consisting of a halogen atom, an alkyl group having 1 to 6 carbon atoms, hydroxyl group, methoxy group, monofluoromethyl group, difluoromethyl group and trifluoromethyl group;

[4] the method according to any one of items [1] to [3] above, wherein R is a group selected from the group consisting of methyl group, phenyl group, 2-methoxyphenyl group, 3-methoxyphenyl group, 4-methoxyphenyl group, 2,4-dimethoxyphenyl group, 3,4-dimethoxyphenyl group, 2-trifluoromethylphenyl group, 3-trifluoromethylphenyl group and 4-trifluoromethylphenyl group;

[5] the method according to item [1] or [2] above, wherein the heteroaryl group is a group selected from the group consisting of pyridyl group, pyrazinyl group, thienyl group, furyl group and thiazolyl group;

[6] the method according to any one of items [1] to [5] above, wherein p is 0, q is 1, r is 1, and X is hydrogen atom;

[7] the method according to any one of items [1] to [6] above, wherein the primary amine is a compound represented by the general formula (3):

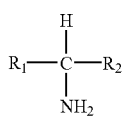

(3)

wherein each of $R_1$ and $R_2$ is independently hydrogen atom, a substituted or unsubstituted alkyl group having 1 to 14 carbon atoms, a substituted or unsubstituted aryl group having 6 to 14 carbon atoms, a substituted or unsubstituted aralkyl group having 1 to 14 carbon atoms, carboxyl group or an alkoxycarbonyl group having 1 to 10 carbon atoms, wherein $R_1$ and $R_2$ may form a ring in a molecule;

[8] the method according to item [7] above, wherein $R_1$ is any one of an alkyl group having 1 to 10 carbon atoms, phenyl group or naphthyl group; and $R_2$ is methyl group, ethyl group, hydroxymethyl group, hydroxyethyl group, carboxyl group, an alkoxycarbonyl group having 1 to 10 carbon atoms or carboxymethyl group;

[9] the method according to any one of items [1] to [8] above, wherein the primary amine is (R)-form;

[10] the method according to any one of items [1] to [9] above, wherein the primary amine is D-alanine, or an alkyl ester of D-alanine, of which alkyl group has 1 to 10 carbon atoms;

[11] the method according to any one of items [1] to [10] above, wherein the primary amine is (R)-1-phenylethylamine, (R)-1-naphthylethylamine, (R)-1-methylpropylamine, (R)-1-methylhexylamine, (R)-2-amino-1-propanol, (R)-1-methylbutylamine, (R)-1-phenylmethylamine, (R)-1-amino-1-phenylethanol, (R)-2-amino-2-phenylethanol, (R)-3-aminoheptane, (R)-1-amino-3-phenylpropane, (R)-2-amino-4-phenylbutane, (R)-2-amino-3-phenylpropanol, (R)-1-methylheptylamine, benzylamine, (S)-2-phenylglycinol, (R)-3-aminophenylbutane, L-phenylalaninol, (R)-2-amino-1-methoxypropane, methyl ester of D-alanine, (R)-1-(3,4-dimethoxyphenyl)-2-aminopropane, (R)-1-phenyl-2-aminopropane, or ethyl ester of D-alanine, or racemic modifications thereof;

[12] the method according to any one of items [1] to [11] above, comprising bringing the ketone compound and the primary amine into contact with a culture, isolated bacterial cells, treated bacterial cells or immobilized bacterial cells, each of which is derived from microorganisms producing transaminase having an activity of stereoselective transamination;

[13] the method according to any one of items [1] to [11] above, comprising bringing the ketone compound and the primary amine into contact with cell-free extracts, partially purified enzymes, purified enzymes or immobilized enzymes, each of which is derived from microorganisms producing transaminase having an activity of stereoselective transamination;

[14] the method according to item [12] or [13] above, wherein the microorganism producing the transaminase is a microorganism belonging to the genus *Arthrobacter*;

[15] the method according to item [14] above, wherein the microorganism belonging to the genus *Arthrobacter* is *Arthrobacter* sp. KNK168 (FERM BP-5228);

[16] the method according to any one of items [12] to [15] above, wherein during the culture of the microorganism capable of producing the transaminase, one or more amines selected from the group consisting of (RS)-1-methylpropylamine, (RS)-1-phenylethylamine, (RS)-1-methylbutylamine, (RS)-3-amino-2,2-dimethylbutane, (RS)-2-amino-1-butanol and (R)- or (RS)-1-(3,4-dimethoxyphenyl)-2-aminopropane are added as an inducer for the enzyme to a medium;

[17] the method according to any one of items [1] to [16] above, wherein the transaminase is allowed to act at a pH range of 5 to 12;

[18] the method according to any one of items [1] to [17] above, comprising acting the transaminase with adding a surfactant or a fatty acid as a reaction accelerator;

[19] a method for preparing an optically active amino compound, comprising stereoselectively transaminating by acting a transaminase on a racemic amino compound represented by the general formula (5):

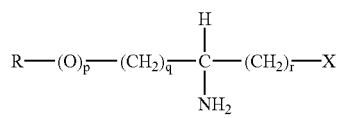

(5)

in the presence of a ketone compound represented by the general formula (4):

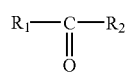

(4)

to thereby give the corresponding optically active amino compound;

[20] a DNA comprising a nucleotide sequence encoding a polypeptide having an activity of stereoselective transamination (simply referred to as "stereoselective transaminase activity");

[21] the DNA according to item [20] above, wherein the polypeptide is derived from a strain belonging to the genus *Arthrobacter*;

[22] a DNA encoding an entire or partial amino acid sequence as shown in SEQ ID NOS:1–4 in Sequence Listing, wherein the DNA encodes a polypeptide having stereoselective transaminase activity;

[23] a DNA comprising an entire or partial nucleotide sequence as shown in SEQ ID NOS:5–7 in Sequence Listing, wherein the DNA encodes a polypeptide having stereoselective transaminase activity;

[24] a DNA comprising a nucleotide sequence resulting from deletion, addition, insertion or substitution of one or more bases in the nucleotide sequence as shown in SEQ ID NOS:5–7 in Sequence Listing, wherein the DNA encodes a polypeptide having stereoselective transaminase activity;

[25] a DNA encoding a polypeptide comprising an amino acid sequence resulting from deletion, addition, insertion or substitution of one or more amino acid residues in the amino acid sequence as shown in SEQ ID NOS:1–4 in Sequence Listing, wherein the polypeptide has stereoselective transaminase activity;

[26] a polypeptide having stereoselective transaminase activity obtainable from a culture of a microorganism belonging to the genus *Arthrobacter*;

[27] a polypeptide comprising a partial amino acid sequence as shown in SEQ ID NO:8, SEQ ID NO:9 or SEQ ID NO:11 in Sequence Listing, and having stereoselective transaminase activity;

[28] a polypeptide comprising an entire or partial amino acid sequence as shown in SEQ ID NOS:1–4 in Sequence Listing, and having stereoselective transaminase activity;

[29] a polypeptide comprising an amino acid sequence resulting from deletion, addition, insertion or substitution of one or more amino acid residues in the amino acid sequence as shown in SEQ ID NOS:1–4 in Sequence Listing, and having stereoselective transaminase activity;

[30] a recombinant DNA comprising the DNA according to any one of items [20] to [25] above;

[31] the recombinant DNA according to item [30] above, wherein the recombinant DNA is capable of expressing a polypeptide encoded thereby in microorganisms, animals or animal cells, or plants or plant cells;

[32] an expression vector resulting from insertion of the recombinant DNA according to item [30] or [31] above for microorganisms, animal cells or plant cells as host cells;

[33] the expression vector according to item [32] above, wherein the expression vector is plasmid pAT28, pAT29 or pAT30;

[34] a transformant obtainable by transforming with the expression vector according to item [32] or [33] above;

[35] the transformant according to item [34] above, wherein the transformant is *Escherichia coli*;

[36] the transformant according to item [35] above, wherein *Escherichia coli* is *E. coli* JM109 (pAT28), *E. coli* JM109 (pAT29), or *E. coli* JM109 (pAT30);

[37] a method for preparing a polypeptide having stereoselective transaminase activity, characterized in culturing or growing the transformant according to any one of items [34] to [36] above, and collecting a polypeptide having stereoselective transaminase activity from the culture medium used in culture or the transformant;

[38] the method according any one of items [1] to [19] above, wherein the polypeptide having stereoselective transaminase activity obtainable by the method according to item [37] above is used as a transaminase;

[39] a DNA capable of hybridizing under stringent conditions to an entire or partial portion of a DNA comprising the nucleotide sequence as shown in SEQ ID NOS:5–7, or to an entire or partial portion of a strand complementary to the DNA, wherein the DNA encodes a polypeptide having stereoselective transaminase activity; and

[40] an oligonucleotide capable of hybridizing with the DNA according to any one of items [20] to [25] above under stringent conditions, wherein the oligonucleotide is usable as a probe or primer.

BRIEF DESCRIPTION OF THE DRAWINGS

FIG. 1 is a graph showing the optimal pH for the present enzyme.

BEST MODE FOR CARRYING OUT THE INVENTION

Figure 2:
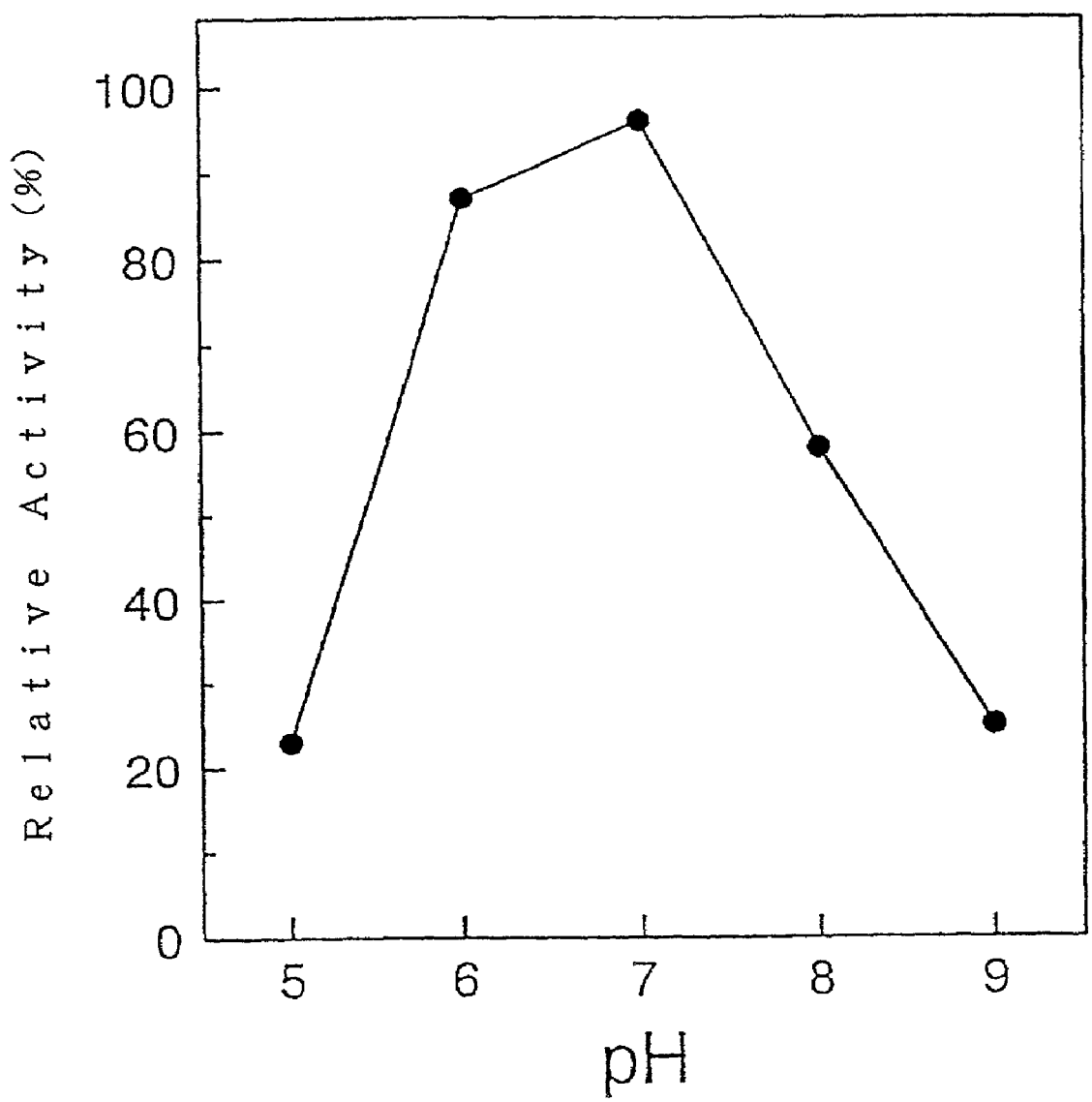
FIG. 2 is a graph showing the pH stability for the present enzyme.

The present invention will be described in detail below. First, the reaction scheme in the present invention is shown as follows.

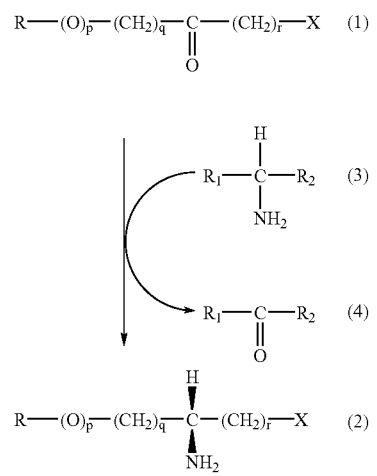

The corresponding optically active amino compound

The present inventors have carried out repeated screening to separate bacteria from domestic soil, the bacteria having an ability of producing (R)-amino compounds in (R)-form specificity using ketones as substrates, and consequently have found that bacteria belonging to the genus *Arthrobacter* have strong activity for catalyzing this reaction. Among them, the bacteriological natures of *Arthrobacter* sp. [named *Arthrobacter* sp. KNK168, and deposited with an accession number FERM BP 5228 with National Institute of Bioscience and Human-Technology, Agency of Industrial Science and Technology (address: 1-3, Higashi 1-chome, Tsukuba-shi, Ibaraki-ken, Japan (zip code: 305-0046)), since Sep. 8, 1995 (date of original deposit)] are shown as follows.

| | |
|---|---|
| Cell Morphology | Rod (Coryne type) |
| Gram Staining | Positive |
| Spore Formation | None |
| Mobility | None |
| Colony Morphology | Colony with round, regular, entire, yellow, smooth, glossy, semi-translucent, convex, and 2 m in diameter (Bennett's agar medium) |
| Growth | |
| (30° C.) | + |
| (37° C.) | − |
| Catalase | + |
| Oxidase | − |

-continued

| | |
|---|---|
| OF Test (glucose) | – (oxidative) |
| Cell Wall | No mycolic acid; diamino acid is lysine. |
| Fatty Acid Analysis | Almost all the acids present are three-branched iso- and anteiso acid. |

The transaminase produced by this bacterium is obviously different from an enzyme of *Brevibacterium linens* IFO12141 used in Nakamichi et al. (*Appl. Microbiol. Biotechnol.*, 33, 634–640 (1990)) and an ω-amino acid transaminase used in Stirling et al. (Japanese Patent Laid-Open No. Hei 3-103192), in which an (S)-amine is used as an amino group donor and the resulting product is an optically active (S)-amino compound, from the aspects that when an (R)-form amine, such as (R)-1-phenylethylamine, is used as an amino group donor and 1-(3,4-dimethoxyphenyl)-2-propanone is used as an amino group acceptor, the resulting product is an optically active (R)-1-(3,4-dimethoxyphenyl)-2-aminopropane, as described in detail below.

Further, the transaminase derived from *Arthrobacter* which can be used in the present invention is different from the above-mentioned enzyme derived from Brevibacterium in many other aspects. For example, there are differences from the aspect that inorganic ammonium salts such as ammonium chloride, and L-amino acids (being (S)-amines) such as glutamic acid and aspartic acid cannot be used as an amino group donor (Table 1).

TABLE 1

| Amino Group Donor | Transaminase of Present Invention | Enzyme Used in Nakamichi et al. |
|---|---|---|
| Inorganic Ammonium Salt | – | + |
| L-Amino Acid | – | + |

In addition, when the transaminase derived from *Arthrobacter* which can be used in the present invention is compared with the ω-amino acid transaminase used in Stirling et al. (Japanese Patent Laid-Open No. Hei 3-103192), in addition to the obvious difference regarding the above-mentioned substrate specificity, there are differences from the aspect that the transaminase derived from *Arthrobacter* does not act on ω-amino acids such as β-alanine and 4-aminobutyric acid; ω-amines such as n-butylamine and putrescine; DL-3-aminobutyric acid, or the like, and the aspect that the transaminase derived from *Arthrobacter* is affected only a little by reaction inhibitors such as hydroxylamine and phenylhydrazine.

In addition, as other enzymes similar to the enzyme used by the present inventors, benzylamine transaminase is disclosed in Okada et al. (Japanese Patent Laid-Open No. Hei 6-178685), wherein the benzylamine transaminase strongly acts on benzylamine in the presence of pyruvic acid to form L-alanine and benzaldehyde. However, the benzylamine transaminase has a similar optical selectivity to that of the above-mentioned enzyme derived from Brevibacterium or to that of the ω-amino acid transaminase from the aspect that the optical activity of the product resulting from the transaminase reaction by this enzyme is that of L-alanine, an (S)-form, and it can be said that the benzylamine transaminase is completely different from the enzyme derived from *Arthrobacter* which can be used in the present invention.

Further, when these enzymes are compared, it seems that there are some differences in influence caused by reaction inhibitors such as phenylhydrazine, D-penicillamine and p-chloromercuribenzoic acid.

The differences with the ω-amino acid transaminase derived from *Pseudomonas* sp. F-1 (*Agric. Biol. Chem.*, 42, 2363–2367 (1978), *Agric. Biol. Chem.*, 43, 1043–1048 (1979), *J. Biol. Chem.*, 258, 2260–2265 (1983)) which have been well studied among the ω-amino acid transaminases, and with the benzylamine transaminase of Okada et al. (Japanese Patent Laid-Open No. Hei 6-178685) are summarized and shown in Table 2. In a case of the transaminase reaction in the present invention, the data of the purified enzyme are used, and in cases of those by other two enzymes, the data of the purified enzymes which are disclosed in each of the literature publication and laid-open patent publication are used. Pyruvic acid is used as an amino group acceptor in all cases.

TABLE 2

| | Transaminase of Present Invention | ω-Amino Acid Transaminase | Transaminase of Okada et al. |
|---|---|---|---|
| Substrate Specificity | | | |
| β-Alanine | 0* | 100* | 0* |
| 4-Aminobutyric acid | 0 | 40 | |
| DL-3-Aminobutyric acid | 0 | 96 | |
| n-Butylamine | 0 | 60 | 0 |
| Benzylamine | 0.8 | 45 | 100 |
| Putrescine | 0 | 55 | 0 |
| β-Phenethylamine | 0 | 54 | 9 |
| Amino Group Donor | | | |
| L-Alanine | – | + | + |
| Inhibitor (1 mM each) (without addition) | 100* | 100* | 100* |
| Hydroxylamine | 17 | 0 | 30 (0.1 mM) |
| Phenylhydrazine | 82 | 6 | 27 |
| D-Penicillamine | 93 | 65 | 0 |
| p-Chloromercuribenzoic acid | 53 | 100 | 9 (0.1 mM) |
| CuSO$_4$ | 44 | | 5 (0.5 mM) |
| Gabaculine | 24 | 0 | |

Remark)
*Numerical values are expressed in relative activity (%).

The activity of the transaminase (intracellular enzyme) which can be used in the present invention on the typical substrates of the ω-aminotransferases is shown in Table 3. In the case of using an ω-amino acid or an ω-amine as an amino group donor, the ω-aminotransferase activity is extremely low, and the transferase used in the present invention does not act on β-alanine which is a typical substrate of ω-amino acid-pyruvic acid aminotransferase. The transferase used in the present invention shows an especially high activity on (R)-1-phenylethylamine. Therefore, it is quite different from the ω-amino transaminase in the substrate specificity.

TABLE 3

| Amino Group Donor | Amino Group Acceptor | Relative Activity (%) |
|---|---|---|
| β-Alanine | Pyruvic acid | 0 |
| 4-Aminobutyric acid | 2-Ketoglutaric acid | 0 |
| 2,5-Diaminovalerate (α,ω-amino acid) | 2-Ketoglutaric acid | 2 |
| DL-Ornithine | 2-Ketoglutaric acid | 0 |
| DL-Lysine | 2-Ketoglutaric acid | 0 |
| Putrescine (α,ω-Diamine) | 2-Ketoglutaric acid | 0 |
| α-2,4-Diaminobutyric acid | Pyruvic acid | 0 |
| Taurine | 2-Ketoglutaric acid | 0 |
| DL-Asparagine | 2-Ketoglutaric acid | 0 |
| DL-Glutamine | 2-Ketoglutaric acid | 0 |
| (R)-1-Phenylethylamine | Pyruvic acid | 100* |

Remark)
*Control.

In a case where the transamination which can be employed in the present invention is carried out, the enzyme expression level is increased by addition of an inducer upon culturing microorganisms. There can be used as the above inducers one or more kinds of amines selected from the group consisting of (RS)-1-methylpropylamine, (RS)-1-phenylethylamine, (RS)-1-methylbutylamine, (RS)-3-amino-2,2-dimethylbutane, (RS)-2-amino-1-butanol, and (R)- or (RS)-1(3,4-dimethoxyphenyl)aminopropane.

The DNA of the present invention comprises a nucleotide sequence encoding a polypeptide having an activity of stereoselective transamination (simply referred to as "stereoselective transaminase activity") Examples of the above DNA include 1) a DNA encoding an entire or partial amino acid sequence as shown in SEQ ID NOS:1–4 in Sequence Listing, wherein the DNA encodes a polypeptide having stereoselective transaminase activity; 2) a DNA comprising an entire or partial nucleotide sequence as shown in SEQ ID NOS:5–7 in Sequence Listing, wherein the DNA encodes a polypeptide having stereoselective transaminase activity; 3) a DNA encoding a polypeptide comprising an amino acid sequence resulting from deletion, addition, insertion or substitution of one or more amino acid residues in the amino acid sequence as shown in SEQ ID NOS:1–4 in Sequence Listing, wherein the DNA encodes a polypeptide having stereoselective transaminase activity; and 4) a DNA comprising a nucleotide sequence resulting from deletion, addition, insertion or substitution of one or more bases in the nucleotide sequence as shown in SEQ ID NOS:5–7 in Sequence Listing, wherein the DNA encodes a polypeptide having stereoselective transaminase activity.

The DNA of the present invention can be cloned by the method described below.

As the method for cloning a transaminase gene, there can be utilized a method employing the activity as an index, a method utilizing an amino acid sequence of the enzyme, and the like. In the present invention, the method of utilizing the amino acid sequence will be described, and as a matter of course, the present invention is not limited to this method. First, the isolation and purification of the transaminase will be described below, and subsequently, the method for cloning the transaminase gene will be described. Further, the expression of the gene (production of transaminase) will be described.

Isolation and Purification of Transaminase

The strains used may be any kinds of strains as long as they produce a polypeptide having stereoselective transaminase activity which stereoselectively converts to the corresponding optically active amino compound using ketones as substrates. For instance, there are exemplified those derived from the strain belonging to the genus *Arthrobacer*. Among them, the isolation and purification of transaminase produced by typical strain *Arthrobacter species* KNK168 (FERM BP-5228) will be described below.

In the culture of KNK168, any kinds of methods may be employed as long as it is a culture method for growing the strain and producing the transaminase. Preferably, the culture method described below can be employed. To a 1.5 liter J medium (5 g/l $KH_2PO_4$, 5 g/l $K_2HPO_4$, 1 g/l NaCl, 1 g/l $MgSO_4 \cdot 7H_2O$, 0.005 g/l $FeSO_4 \cdot 7H_2O$, 0.001 g/l $ZnSO_4 \cdot 7H_2O$, 0.001 g/l $MnCl_2 \cdot 4H_2O$, 0.0005 g/l $CuSO_4 5H_2O$ (pH 7.5), 40 g/l glycerol, 3 g/l yeast extract powder, 20 g/l PRO-EX (BANSYU CHOMIRYO CO., LTD.), a pH being adjusted to 7.5) in a 2 liter-mini jar, is inoculated a 30 ml culture medium prepared by overnight preculture in the same medium, and the bacterium is cultured at 30° C. at 0.5 vvm and 450 rpm for 43 hours with adjusting the culture to a pH of 7.5. Incidentally, from the start of culturing, (RS)-1-methylpropylamine filtered by a microorganisms exclusion filter is added so as to have a final concentration 4 g/l after 14 hours.

The cells are harvested from the resulting culture by centrifugation, and the like, and the harvested cells are suspended in a suitable buffer, for example, 20 mM potassium phosphate buffer (pH 6.8) containing 0.01% 2-mercaptoethanol. The cells are disrupted by the treatment with Dynomill (Switzerland), and the like, and the supernatant is obtained by centrifugation. Protamine sulfate is added to this supernatant so as to give a concentration 50 mg/ml, and nucleic acids are removed. The transaminase is precipitated by salting out with ammonium sulfate, and the like. As a preferable embodiment, a fraction obtained by salting out between a concentration 30% and 60% saturated ammonium sulfate is collected. The fraction is dissolved in the above-mentioned buffer, and dialyzed against the same buffer, and thereafter, the dialyzed fraction is further purified with an anion exchange resin. As a preferable embodiment, the composition of the buffer is adjusted to have 20% (v/v) glycerol, 0.3 M NaCl, and 20 µM pyridoxal phosphate, and thereafter applied to a DEAE-Sepharose, Fast-Flow (Pharmacia LKB) column equilibrated with this solution, and thereafter eluted with 0.3 to 0.5 M NaCl linear concentration gradient. The active fraction is collected and can be further purified by hydrophobic chromatography. Preferably, Phenyl-Sepharose (Pharmacia LKB) is used. After the active fraction is dialyzed, ammonium sulfate is added thereto so as to give a concentration 0.2 M. Thereafter, the resulting active fraction is applied to a Phenyl-Sepharose column equilibrated with the above buffer containing 0.2 M ammonium sulfate in place of 0.3 M NaCl, and thereafter eluted with 0.2 to 0 M ammonium sulfate linear concentration gradient. After the concentration of ammonium sulfate in this active fraction is adjusted to 0.6 M, the resulting active fraction is applied to a Butyl-Sepharose (Pharmacia LKB) column equilibrated with the above buffer containing 0.6 M ammonium sulfate in place of 0.2 M ammonium sulfate. The transaminase preparation can be obtained by collecting the above active fraction, and concentrating the collected fraction with procedures such as ultrafiltration, the transaminase preparation being purified to a substantially homogenous level in SDS-polyacrylamide gel electrophoresis.

Amino Acid Sequence Analysis

Subsequently, as to the purified transaminase, the information concerning partial amino acid sequences thereof is obtained. The partial amino acid sequence can be determined by Edman degradation method, wherein the amino acid sequence can be determined by utilizing a vapor phase protein sequencer (Applied Biosystems, Model "470A"), and the like. The N-terminal amino acid sequence can be determined by carrying out determination of an amino acid sequence directly by using the purified transaminase. Alternatively, an internal amino acid sequence can be obtained by acting a proteolytic enzyme having a high specificity, for instance, N-tosyl-L-phenylalanyl chloromethyl ketone (TPCK) derived from bovine spleen, V8 protease derived from *Staphylococcus aureus* V8 strain to carry out limited hydrolysis, separating and purifying the resulting peptide fragment by using reverse phase HPLC, and thereafter determining the amino acid sequence.

The transaminase can be cloned on the basis of the information of the partial amino acid sequences as obtained above.

Cloning of Transaminase Gene

As the method for cloning the above gene on the basis of the partial amino acid sequence of the transaminase, there can be employed generally usable PCR methods, hybridization methods, or a combination of these methods.

a) Preparation of Chromosomal DNA Library

As the preparation of the chromosomal DNA library, Maniatis et al. (*Molecular Cloning*, T. Maniatis et al., Cold Spring Harbor Press) describe a method using a plasmid vector, λ-phage vector, or a cosmid vector is used. The chromosomal DNA of KNK168 can be prepared by the method in accordance with *Current Protocol in Molecular Biology* (F. Ausubel et al., Willy Interscience), or the like. The chromosomal DNA obtained is partially digested with various restriction enzymes, for instance, Sau3AI and TthHB8I. Thereafter, a chromosomal DNA fragment which has an appropriate size for incorporation into a vector is purified by such means as agarose gel electrophoresis or sucrose density gradient centrifugation. The insertion site in the vector must be appropriately selected in accordance with the restriction enzymes used in the preparation of the chromosomal DNA. For instance, when the chromosomal DNA is prepared by digesting with Sau3AI, the restriction enzyme is preferably BamHI. In the λ-phase vector, an about 8 kb to about twenty and several kb DNA fragment can be inserted, and in the cosmid vector, a further larger DNA fragment can be inserted. In the library using a plasmid, it is advantageous to insert a large DNA fragment from the viewpoint of carrying out screening as described below, but a chromosomal DNA fragment of any size may be inserted thereinto. As the plasmid vectors, pUC18, pUC19, pUC119, pTV118N, and the like can be favorably used, and the plasmid vectors are not particularly limited thereto.

Any of the above may be used as chromosomal DNA libraries. The case where the plasmid is used will be described in detail below.

b) Transformation

A host is transformed by introducing the recombinant plasmid prepared by the method described above into the host. When *Escherichia coli* is used as a host, the host *Escherichia coli* may be any of wild-type strains or mutants as long as it has competency. The method for transformation can be carried out by a usually employed method, including, for instance, a method by T. Maniatis et al. (*Molecular Cloning*, Cold Spring Harbor Press).

The transformant is screened, for instance, in the case of pUC19, as a colony growing on a plated medium containing ampicillin. Further, the transformant in which the chromosomal DNA is inserted can be obtained by screening a colony showing resistance to ampicillin and exhibiting a white color on a plate containing 5-bromo-4-chloro-3-indolyl-β-D-galactopyranoside (X-Gal) and isopropyl-β-D-thiogalactopyranoside (IPTG).

The chromosomal DNA library can be prepared using the plasmid vector as described above.

c) Preparation of Probe

The DNA used as a probe or primer for use in hybridization or PCR is required to have a high specificity. When the probe or primer is prepared based on the partial amino acid sequence of the transaminase, usually a single-stranded DNA corresponding to the amino acid sequence is prepared. The codon corresponding to each amino acid may vary from those of a single kind as in the case of methionine or tryptophan, to those of six kinds as in the case of leucine. In order to increase the specificity of the probe or primer, it is necessary that the chain length of the probe or primer is lengthened, and that the kinds of the nucleotide sequence corresponding to the amino acid sequence are made small. As a preferable example, it is desired that the nucleotide comprises a chain length of 15 nucleotides or more, which comprises a mixture of 100 kinds to not more than 200 kinds of single-stranded DNAs, but not limited thereto as long as the desired specificity can be obtained. In addition, there may be a case where inosine is introduced into sites corresponding to a plurality of bases to be used as a probe or primer. These DNAs can be synthesized by a DNA synthesizer.

When the transaminase is cloned by colony hybridization, 5'-terminal of the synthesized probe is radiolabeled or fluorescence-labeled. As an example of the radiolabeling, a probe having high specific activity can be prepared by using [γ-$^{32}$P]-ATP and MEGALABEL™ (manufactured by Takara Shuzo Co., Ltd.).

Two primers at N-terminal end and internal portion are synthesized as described above on the basis of the partial amino acid sequences. PCR reaction is carried out by using a chromosomal DNA as a template, whereby making it possible to amplify a part of the transaminase gene. The gene amplified as above is radiolabeled or fluorescence-labeled to be subjected to colony hybridization using the labeled gene as a probe. As an example of the radiolabeling, a probe having high specific activity can be prepared by using [α-$^{32}$P]-dCTP and Random Primer DNA Labeling kit Ver.2 (manufactured by Takara Shuzo Co., Ltd.). Here, it is confirmed that the PCR-amplified DNA is a part of the transaminase gene by determining the nucleotide sequence of the above DNA by the method for determining the nucleotide sequence of the DNA described below, and comparing the amino acid sequence deduced from the above nucleotide sequence with the previously obtained partial amino acid sequence.

d) Cloning of Transaminase Gene by Colony Hybridization

The transaminase gene is cloned by colony hybridization using the plasmid library and the probe. As the colony hybridization, there can be utilized the method of T. Maniatis et al. (*Molecular Cloning*, Cold Spring Harbor Laboratory Press).

When the radiolabeled or fluorescence-labeled, synthetic DNA probe corresponding to the partial amino acid sequence is utilized, it is necessary to set the hybridization temperature, the washing temperature, and the salt concentration in consideration of Tm value of the DNA for each probe.

When the DNA fragment amplified by PCR is utilized as a probe, since its chain length is relatively long, the temperatures for hybridization and washing of 60° to 65° C. are likely to be employed in many cases.

Whether or not a desired clone is obtained can be determined by extracting a plasmid DNA from a positive clone screened as described above, determining a nucleotide sequence, and comparing an amino acid sequence deduced from the nucleotide sequence with the internal amino acid sequence.

One kind of the polypeptide is translated from the transaminase gene cloned as described above, and the codon corresponding to each amino acid may vary from 1 to 6 kinds. Therefore, there are a wide variety of genes corresponding to the amino acid sequence of the polypeptide. In addition, there are a wide variety of genes encoding a polypeptide in which substitution, deletion, insertion or addition of amino acids is introduced into the amino acid sequence of the polypeptide, the polypeptide having stereoselective transaminase activity. Furthermore, although the genes which respectively encode a polypeptide having stereoselective transaminase activity owned by organisms other than that to which the above gene is cloned are not completely the same as the amino acid sequence, there exist homologies in the amino acid sequence and the nucleotide sequence.

The hybridization method can be utilized as a method for experimentally detecting the homology of the nucleotide sequence, wherein the above transaminase genes is included as a gene capable of hybridizing to an entire or partial portion of the above transaminase gene. Therefore, a gene capable of hybridizing to an entire or partial portion of the above transaminase gene is encompassed in the present invention.

Concretely, there can be cited a DNA capable of hybridizing under stringent conditions to an entire or partial portion of the DNA as shown in SEQ ID NOS:5–7, or to an entire or partial portion of complementary strand thereto, wherein the DNA capable of hybridizing thereto encodes a polypeptide having stereoselective transaminase activity.

In addition, the oligonucleotide of the present invention is capable of hybridizing with the DNA according to the present invention under stringent conditions, wherein the oligonucleotide is usable as a probe or primer.

As the hybridization, there can be utilized the method of T. Maniatis et al. (*Molecular Cloning*, Cold Spring Harbor Laboratory Press), and the like. The conditions for hybridization can be appropriately selected by the length of the transaminase gene to be used as a probe, of which specificity is determined by the hybridization temperature, the washing temperature, and the salt concentration of the washing solution, and the combination with the subject DNA. Hybridization is carried out under stringent conditions. Concretely, the hybridization temperature and the washing temperature are 30° C. or more, and the salt concentration of the washing solution is such that a washing solution having a salt concentration of not more than 2×SSC or 2×SSPE.

e) Determination of Nucleotide Sequence of DNA

The nucleotide sequence of DNA can be determined by Sanger method or Maxam-Gilbert method (Molecular Cloning, T. Maniatis et al., Cold Spring Harbor Laboratory Press) Further, the DNA nucleotide sequence can also be determined by ABI373A DNA Sequencer using DNA Sequencing Kit (Dye Terminater Cycle Sequencing Ready Reaction) as made commercially available by K.K. Perkin-Elmer Japan.

The structure of the transaminase gene can be elucidated by analyzing the determined nucleotide sequence, and comparing the amino acid sequence deduced from the nucleotide sequence with the previously obtained partial amino acid sequence.

Expression of Transaminase Gene

In order to produce the transaminase, there can be utilized as a host microorganisms, animals or animal cells, plants or plant cells, and the like. The host is transformed after insertion of a transaminase gene into a preferable expression vector for each host. The resulting transformed strain is cultured, whereby producing the transaminase.

As a preferable embodiment, *Escherichia coli* can be used as a host. As the expression vector, there can be utilized an expression vector utilizing the promoter for lactose operon, for instance, pUCNT (WO 94/03613); an expression vector utilizing λ-phage $P_L$ promoter, for instance, pPL-lambda (Pharmacia LKB); and an expression vector utilizing Tac promoter, for instance, pKK223-3 (Pharmacia LKB).

As the transaminase gene to be inserted, a fragment including the translational initiation codon to termination codon of the enzyme can be used. Preferably, it is desired not to contain surplus DNAs at each of upstream and downstream of the above gene, and the gene is not limited thereby. In addition, there may be some cases where the translational initiation codon is GTG, TTG, or the like in place of ATG depending upon the gene. In such cases, it is more preferable that the initiation codon is changed to ATG for the sake of expression in *Escherichia coli*.

In summary, the polypeptide having stereoselective transaminase activity of the present invention can be obtained by, for instance, culturing the microorganisms belonging to the genus *Arthrobacter*. Examples of the polypeptide include 1) a polypeptide comprising a partial amino acid sequence as shown in SEQ ID NO:8, SEQ ID NO:9 or SEQ ID NO:11 in Sequence Listing, and having stereoselective transaminase activity; 2) a polypeptide comprising an entire or partial amino acid sequence as shown in SEQ ID NOS: 1–4 in Sequence Listing, and having stereoselective transaminase activity; and 3) a polypeptide comprising amino acids resulting from deletion, addition, insertion or substitution of one or more amino acid residues in the amino acid sequence as shown in SEQ ID NOS:1–4 in Sequence Listing, and having stereoselective transaminase activity.

The recombinant DNA of the present invention comprises the DNA of the present invention described above. Examples of the recombinant DNA are preferably an expression vector capable of expressing an encoded polypeptide in microorganisms, animals or animal cells, or plants or plant cells. For instance, as one example, the expression vector includes plasmid pAT28, pAT29 or pAT30, each of which is a recombinant DNA in which a DNA comprising a nucleotide sequence encoding a polypeptide having stereoselective transaminase activity is inserted into pUCNT. The above plasmid can be obtained by the method described in Examples.

The transformant of the present invention is obtainable by transforming with the expression vector of the present invention described above. Examples of the transformant include a transformant obtained by transforming *Escherichia coli* (hereinafter simply *E. coli*) JM109 or HB101. Concrete examples of *Escherichia coli* used as a transformant include *E. coli* JM109 (pAT28), *E. coli* JM109 (pAT29), or *E. coli* JM109 (pAT30).

The transformant can be obtained by transforming with the expression vector of the present invention described above by a known method.

The method for preparing a polypeptide having stereoselective transaminase activity of the present invention is characterized by culturing or growing the transformant of the present invention described above, and collecting a polypeptide having stereoselective transaminase activity from the culture medium used in culture or the transformant. The transaminase can be efficiently produced by determining optimal conditions for the medium composition, the pH of the medium, the culture temperature, the use of IPTG or absence thereof and the addition period of time, the culture period of time, and the like. The transaminase which can be obtained by the method for preparing the polypeptide of the present invention can be preferably used in a method for preparing an optically active amino compound of the present invention.

A usual method is employed in order to purify the polypeptide having stereoselective transaminase activity from the culture of the transformant. When the transformant accumulates the polypeptide within the cells as in the case of *Escherichia coli*, after the termination of culture, the transformant is harvested by centrifugation, or the like, disrupted by ultrasonication, or the like, and thereafter the disrupted product is subjected to centrifugation, or the like, to give a cell-free extract. The resulting cell-free extract is purified by general protein purification methods such as salting out or various chromatographies such as ion exchange, gel filtration, hydrophobic and affinity chromatographies. There may be some cases where the expression product is secreted to outside of the transformant depending upon the host-vector system employed, in which case the expression product may be similarly purified from the culture supernatant.

In addition, when a host is *Escherichia coli*, there may be a case where an expression product is formed as an insoluble inclusion body. In this case, after the termination of culture, the cells are harvested by centrifugation, and the harvested cells are disrupted by ultrasonication, or the like. Thereafter, an insoluble fraction comprising an inclusion body is collected by centrifugation, or the like. After washing the inclusion body, the inclusion body is solubilized with a usually employed protein solubilizer, for instance, urea, guanidine hydrochloride, or the like, and purified, as occasion demands by carrying out various chromatographies such as ion exchange, gel filtration, hydrophobic and affinity chromatographies, and thereafter carrying out refolding procedures employing a dialytic method or dilution method, to give a transaminase having an activity.

The transaminase used in the present invention can be used in various forms. In other words, not only cultured microorganisms, separated bacterial cells and treated bacterial cells, but also cell-free extracts, partially purified enzymes, purified enzymes, and the like can be used. Further, immobilized products of these cells, immobilized products of the treated bacterial cells, immobilized products of enzyme proteins to immobilizing carriers (for example, anionic exchange resins) and the like can be also used. Here, the immobilization can be carried out by conventional methods (for example, Japanese Patent Laid-Open No. Sho 63-185382).

Supporting materials which can be used in the immobilization include various kinds of anionic exchange resins, such as various amines, ammonium salts and diethanolamine type resins having functional groups. Suitable examples thereof include phenol-formaldehyde anionic exchange resins such as Duolite A568 and DS17186 (registered trademark of Rohm and Haas Company); polystyrene resins, such as Amberlite IRA935, IRA945, and IRA901 (registered trademark of Rohm and Haas Company), Lewatit OC1037 (registered trademark of Bayer A. G.), and Diaion EX-05 (registered trademark of Mitsubishi Chemical Corporation), and the like. In addition, supporting materials, such as DEAE-cellulose, can be used.

Further, cross-linking agents are usually used in order to make the adsorption of enzyme more firm and stable. A preferable example of the cross-linking agents includes glutaraldehyde. The enzymes used include purified enzymes, as well as enzymes at various levels of the purification, such as partially purified enzymes, solutions of disrupted cells, and cell-free extracts.

For preparation of the immobilized enzyme, conventional preparation methods may be employed, including, for example, a method wherein the cross-linking treatment is carried out after adsorption of an enzyme to a supporting material.

The amino acceptors used in the present invention include ketone compounds represented by the general formula (1):

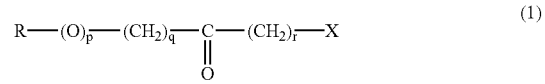

wherein p is 0 or 1; q is an integer of 0 to 8; r is an integer of 0 to 4; R is any one of a substituted or unsubstituted aryl group having 6 to 14 carbon atoms, a heteroaryl group having 4 to 12 carbon atoms, carboxyl group, an alkoxycarbonyl group having 1 to 6 carbon atoms, methyl group or hydrogen atom; and X is any one of hydroxyl group, carboxyl group, an alkoxycarbonyl group having 1 to 6 carbon atoms or hydrogen atom.

Examples of the substituted aryl group include an aryl group substituted by one or more substituents selected from the group consisting of a halogen atom, an alkyl group having 1 to 6 carbon atoms, hydroxyl group, methoxy group, monofluoromethyl group, difluoromethyl group and trifluoromethyl group at one or more sites. Concretely, there can be cited groups selected from the group consisting of 2-methoxyphenyl group, 3-methoxyphenyl group, 4-methoxyphenyl group, 2,4-dimethoxyphenyl group, 3,4-dimethoxyphenyl group, 2-trifluoromethylphenyl group, 3-trifluoromethylphenyl group and 4-trifluoromethylphenyl group.

Examples of the heteroaryl group include groups selected from the group consisting of pyridyl group, pyrazinyl group, thienyl group, furyl group and thiazolyl group.

Among the ketone compounds represented by the general formula (1), a 1-aryl-2-propanone wherein p is 0, q is 1, r is 1, and X is hydrogen atom is particularly preferable. More specifically, preferable are compounds wherein the aryl group in the 1-aryl-2-propanone mentioned above is phenyl group, 2-methoxyphenyl group, 3-methoxyphenyl group, 4-methoxyphenyl group, 2,4-dimethoxyphenyl group, 3,4-dimethoxyphenyl group, 2-trifluoromethylphenyl group, 3-trifluoromethylphenyl group and 4-trifluoromethylphenyl group.

In addition, a 1-methoxy-2-propanone, wherein in the general formula (1), R is methyl group, p is 1, q is 1, r is 1, and X is hydrogen atom, is preferable. Further, pyruvic acid, wherein in the general formula (1), p is 0, q is 1, r is 0, R is hydrogen atom, and X is carboxyl group or an alkyl ester thereof, is also preferable.

The amino group donor used in the present invention as a substrate is a primary amine, and examples thereof include achiral or racemic or optically active amino acid compounds represented by the general formula (3):

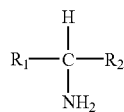

(3)

In the formula, each of $R_1$ and $R_2$ is independently hydrogen atom, a substituted or unsubstituted alkyl group having 1 to 14 carbon atoms, a substituted or unsubstituted aryl group having 6 to 14 carbon atoms, a substituted or unsubstituted aralkyl group having 1 to 14 carbon atoms, carboxyl group or an alkoxycarbonyl group having 1 to 10 carbon atoms, wherein $R_1$ and $R_2$ may form a ring in a molecule.

More specifically, preferable are the primary amines wherein $R_1$ is any one of an alkyl group having 1 to 10 carbon atoms, phenyl group or naphthyl group; and $R_2$ is methyl group, ethyl group, hydroxymethyl group, hydroxyethyl group, carboxyl group, an alkoxycarbonyl group having 1 to 10 carbon atoms or carboxymethyl group.

Concrete examples of the primary amines include, for instance, (R)-1-phenylethylamine, (R)-1-naphthylethylamine, (R)-1-methylpropylamine, (R)-1-methylhexylamine, (R)-2-amino-1-propanol, (R)-1-methylbutylamine, (R)-1-phenylmethylamine, (R)-1-amino-1-phenylethanol, (R)-2-amino-2-phenylethanol, (R)-3-aminoheptane, (R)-1-amino-3-phenylpropane, (R)-2-amino-4-phenylbutane, (R)-2-amino-3-phenylpropanol, (R)-1-methylheptylamine, benzylamine, (S)-2-phenylglycinol, (R)-3-aminophenylbutane, L-phenylalaninol, (R)-2-amino-1-methoxypropane, D-alanine, an alkyl ester of D-alanine of which alkyl group has 1 to 9 carbon atoms (for instance, methyl ester of D-alanine, ethyl ester of D-alanine, and the like), (R)-1-(3,4-dimethoxyphenyl)-2-aminopropane, (R)-1-phenyl-2-aminopropane, or the like. In addition, there can be also cited racemic forms of these compounds as the primary amine.

The method of the present invention comprising acting the transaminase described above having an activity of stereoselectively transaminating on the ketone compound described above in the presence of the primary amine mentioned above, whereby obtaining a desired optically active amino compound.

Examples of the method for acting the enzyme protein on a ketone compound include a method comprising bringing the ketone compound and the primary amine into contact with a culture, isolated bacterial cells, treated bacterial cells, or immobilized cells, each of which is derived from microorganisms producing the enzyme protein; and a method comprising bringing the ketone compound and the primary amine into contact with cell-free extracts, partially purified enzyme proteins, purified enzyme proteins, or immobilized enzyme proteins, each of which is derived from microorganisms producing the enzyme protein.

The concentrations of the substrates used in the reaction are as follows. It is preferred that the concentration of the amino group acceptor is from 0.1 to 10%, preferably from 3 to 5%. Regarding the concentration of the amino group donor, it is preferred that the concentration of mainly an (R)-form, in the case of chiral amine, is about 80 to 150 mol % to the amino group acceptor. In addition, racemic amino compounds can be also used as amino group donors. In such cases, however, twice the concentration as that of the optically active form is needed.

The pH when acting the transaminase is preferably a pH of from 5.0 to 12.0, more preferably a pH of from 7.0 to 10.0. The temperature during the reaction is usually from 25° to 40° C., preferably from 30° to 35° C.

Further, when acting the transaminase, the yield of reaction may be increased by adding a surfactant, including sodium dodecyl sulfate (SDS), Triton X-100, cetyl trimethylammonium bromide (CTAB), or the like, or a fatty acid, including linoleic acid, oleic acid, or the like, as reaction accelerators. It is preferable that the amount of the surfactant or fatty acid added is such that the amount is from 0.1 to 10% by weight of the reaction mixture containing the ketone compound, the primary amine, transaminase, and the like.

Concrete examples of the amino compounds, which are prepared by the method of the present invention, include, for instance, (R)-1-phenyl-2-aminopropane, (R)-1-phenyl-3-aminobutane, (R)-1-(3,4-dimethoxyphenyl)-2-aminopropane, (R)-3-(trifluoromethylphenyl)-2-aminopropane, (R)-3-(p-methoxyphenyl)-2-aminopropane, (R)-4-(p-methoxyphenyl)-2-aminobutane, (R)-4-(3',4'-methylenedioxyphenyl)-2-aminobutane, (R)-4-(p-hydroxyphenyl)-2-aminobutane, (R)-2-amino-1-methoxypropane, and the like.

According to the method for preparing the optically active amino compound of the present invention, for example, in a case where 1-(3,4-dimethoxyphenyl)-2-propanone used as an amino group acceptor and (R)-1-phenylethylamine used as an amino group donor, each having a concentration of 3%, are reacted by using *Arthrobacter* species KNK168 (FERM BP-5228) for about 20 hours, 75% or more of 1-(3,4-dimethoxyphenyl)-2-propanone can be converted to (R)-1-(3,4-dimethoxyphenyl)-2-aminopropane with an optical purity of 99% ee or more by the transamination.

The quantification of the optically active amino compound obtained as the reaction product can be carried out by means of high-performance liquid chromatography. For example, the quantitative analysis can be carried out by separating the reaction mixture by using a reversed phase column (Cosmosil $5C_{18}$-AR, NACALAI TESQUE, INC., and the like) and using 25% acetonitrile as a mobile phase, and the detected absorptions at 210 nm were compared with the control. In addition, there are several methods for measuring the optical purity. For example, the analysis of the optical purity can be carried out by binding the resulting optically active amino compound with N-carboxy-L-leucine anhydride, and the like, to form a diastereomer, and thereafter separating and quantifying this diastereomer by the above-mentioned high-performance liquid chromatography method.

The method for separating the desired optically active amino compound after the reaction can be carried out by a usual method in which extraction with an organic solvent and distillation are combined. For example, ethyl acetate, toluene, and the like can be used as the extraction solvent.

First, the reaction solution is made acidic and then extracted to remove the ketones. Thereafter, the reaction solution is made alkaline, and then extracted to separate the amines including the desired compound. Further, the desired optically active amino compound can be isolated by further means of distillation of the extracted fraction.

Since the transaminase used in the present invention has an activity of stereoselective transamination, when the enzyme protein is allowed to act on the racemic amino compound represented by the general formula (5):

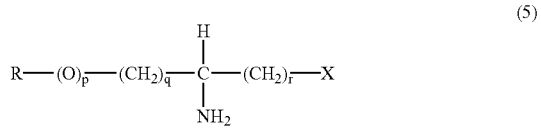

in the presence of the ketone compound (amino group acceptor) represented by the general formula (4):

only one of steric amino compound is selectively converted to ketone compounds, and its enantiomer remains unchanged to be collected as the amino compound. Therefore, the corresponding optically active amino compounds can be easily prepared from racemic amino compounds by using the transaminase utilized in the present invention.

For example, in a case where racemic forms of 1-(3,4-dimethoxyphenyl)-2-aminopropane or 2-amino-1-methoxypropane as an amino group donor are reacted with pyruvic acid used as an amino group acceptor using *Arthrobacter* species KNK168 (FERM BP-5228), the (R)-form amino compound is converted to the ketone form by the transamination, so that the (S)-form amino compound can be obtained at about 50% yield in a concentrated state up to a high optical purity level.

The present invention will be described more concretely hereinbelow by means of the working examples, without intending to restrict the scope of the present invention thereto.

EXAMPLE 1

Each 2 g of soil samples collected at various places in this country was suspended in 5 ml physiological saline. The 0.2 ml supernatant thereof was added to a 4 ml S medium (2 g/L KH$_2$PO$_4$, 2 g/L K$_2$HPO$_4$, 0.3 g/L MgSO$_4$.7H$_2$O, 5 g/L glycerol, 3 g/L NaCl, 1 g/L yeast extract powder, 0.004 g/L FeSO$_4$.7H$_2$O, 0.0005 g/L ZnSO$_4$.7H$_2$O, 0.0005 g/L MnCl$_2$.4H$_2$O (pH 7.5) after a treatment of autoclaving; and 2-oxoglutaric acid or pyruvic acid and (R)-1-(3,4-dimethoxyphenyl)-2-aminopropane, each of which is filtrated by a microorganisms exclusion filter, being added so as to give final concentrations 1.5 g/L and 1.0 g/L, respectively) The resulting culture was subjected to an enrichment culture at 30° C. for 3 to 7 days. Each 0.2 ml culture in which the bacteria were grown was spread on an S-medium plate containing 1.5% agar, and the colonies were grown by culturing at 30° C. The grown colonies were subjected to shaking culture in the S-medium, respectively. After harvesting the cells, they were suspended in a 0.25 ml reaction mixture containing 0.1 M carbonic acid buffer (pH 8.5), 50 mM pyruvic acid and 30 mM (R)-1-(3,4-dimethoxyphenyl)-2-aminopropane, and the components were reacted with stirring at 30° C. for 24 hours.

The resulting reaction mixture was separated by thin-layer chromatography (Kieselgel 60F254 (Merck)); developing solvent being diethyl ether:methanol:aqueous ammonia solution (27%)=50:50:2). The decrease of the substrates was detected by ninhydrin, and the formation of the resulting product, 1-(3,4-dimethoxyphenyl)-2-propanone, was detected by 0.4% 2,4-dihydrophenyl hydrazine. With regard to the strains in which the formation of the desired products was confirmed, the presence or absence of the (R)-selective transamination activity was examined by carrying out its reverse reaction. Specifically, the cultured cells were added to a reaction mixture containing 0.6% 1-(3,4-dimethoxyphenyl)-2-propanone and 0.6% (R)-1-phenylethylamine, and the mixture was reacted at 30° C. for 2 days. As a result, there were found that (R)-1-(3,4-dimethoxyphenyl)-2-aminopropane was formed, and that the *Arthrobacter* species KNK168 strain had the (R)-selective transamination activity.

EXAMPLE 2

When culturing the *Arthrobacter* species KNK168 strain by the method described in Example 1, (RS)-1-methylpropylamine, (RS)-1-methylbutylamine, (RS)-3-amino-2,2-dimethylbutane, (RS)-2-amino-1-butanol, or (RS)-1-phenylethylamine was added to the medium in place of (R)-1-(3, 4-dimethoxyphenyl)-2-aminopropane ((R)-DMA). The cells were separated from the culture, and the reaction was carried out at 30° C. for 20 hours using the above cells in a reaction mixture containing 1% 1-(3,4-dimethoxyphenyl)-2-propanone and 1% (RS)-1-methylpropylamine. As a result, an increase of the reactivity was observed as shown in Table 4.

TABLE 4

| Inducer | (R)-DMA Formed (%) |
|---|---|
| (RS)-1-Methylpropylamine | 22.3 |
| (RS)-1-Methylbutylamine | 13.0 |
| (RS)-1-Phenylethylamine | 8.0 |
| (RS)-3-Amino-2,2-dimethylbutane | 18.6 |
| (RS)-2-Amino-1-butanol | 12.9 |
| (R)-DMA | 0.9 |
| No Addition | 0.3 |

EXAMPLE 3

The *Arthrobacter* species KNK168 strain was inoculated to an R medium (5 g/L KH$_2$PO$_4$, 5 g/L K$_2$HPO$_4$, 3 g/L NaCl, 1 g/L MgSO$_4$.7H$_2$O, 0.005 g/L FeSO$_4$.7H$_2$O, 0.001 g/L ZnSO$_4$.7H$_2$O, 0.001 g/L MnCl$_2$.4H$_2$O (pH 7.5) after a treatment of autoclaving, 15 g/L glycerol, 2 g/L yeast extract powder, 8 g/L PRO-EX (BANSYU CHOMIRYO CO., LTD.); pyruvic acid and (RS)-1-methylpropylamine, filtrated by a microorganisms exclusion filter, being added so as to give final concentrations 1.6 g/L and 2.0 g/L, respectively, and being adjusted to pH 7.2), and then subjected to shaking culture at 30° C. for 24 hours. The cultured cells were harvested by centrifugation, and the harvested cells were suspended in a reaction mixture (pH 8.5) containing 1% 1-(3,4-dimethoxyphenyl)-2-propanone, 0.1% Triton X-100, and 1% an amino group donor shown in Table 5. The mixture was reacted at 35° C. for 20 hours. As shown in Table 5, it was found that (RS)-1-phenylethylamine, (RS)-1-methylbutylamine, (RS)-1-methylpropylamine, (RS)-2-aminopentane, (RS)-1-methylbutylamine, and the like, functioned as amino group donors, among which (RS)-1-phenylethylamine was most highly preferable.

TABLE 5

| Amino Group Donor | (R)-DMA Formed (%) |
|---|---|
| (RS)-1-Phenylethylamine | 61.3 |
| (RS)-1-Methylbutylamine | 54.7 |
| (RS)-1-Methylpropylamine | 28.2 |
| (RS)-1-Methylbutylamine | 56.9 |
| (RS)-2-Amino-1-propanol | 9.6 |
| (RS)-2-Amino-2-phenylethanol | 48.4 |
| (RS)-2-Amino-3-phenylpropanol | 22.7 |
| (RS)-2-Amino-4-phenylbutane | 27.6 |
| (RS)-1-Amino-2-phenylpropane | 1.8 |
| (RS)-1-Phenylmethylamine | 3.1 |
| (RS)-3-Aminoheptane | 7.4 |
| (R)-1-Naphthylethylamine | 34.2 |
| D-Alanine methyl ester | 3.5 |
| D-Alanine ethyl ester | 4.2 |
| D-Alanine | 3.0 |

EXAMPLE 4

The cells obtained by culturing the *Arthrobacter* species KNK168 strain in the R medium were suspended in a reaction mixture containing 2% 1-(3,4-dimethoxyphenyl)-2-propanone and 4% (RS)-1-phenylethylamine. The surfactants and fatty acids shown in Table 6 were added thereto, and the mixture was reacted at 30° C. at a pH of 8.5 for 20 hours. As a result, it was found that the yield of the reaction product was increased by addition of sodium dodecyl sulfate, linoleic acid, oleic acid, or the like to the reaction mixture.

TABLE 6

| Additives (%) | | (R)-DMA Formed (%) |
|---|---|---|
| Triton X-100 | 0.1 | 31.6 |
| | 0.5 | 34.0 |
| Sodium dodecyl sulfate | 0.1 | 45.3 |
| | 0.5 | 42.2 |
| | 1.0 | 46.3 |
| | 2.0 | 50.1 |
| | 3.0 | 51.9 |
| | 4.0 | 53.1 |
| Cetyl trimethyl ammonium bromide (CTAB) | 0.1 | 29.1 |
| Linoleic Acid | 2.9 | 45.1 |
| Oleic Acid | 2.9 | 44.9 |
| (No Addition) | | 28.1 |

EXAMPLE 5

Using the cells obtained by culturing the *Arthrobacter* species KNK168 strain in the R medium, the reaction was carried out at 35° C. for 20 hours, at the pH variable from 7.5 to 9.5, the reaction mixture containing 2% 1-(3,4-dimethoxyphenyl)-2-propanone, 1.4% (RS)-1-phenylethylamine, and 0.1% sodium dodecyl sulfate. As a result, the yield of the reaction product at a pH of 8.5 to 9.0 was favorable as shown in Table 7.

TABLE 7

| Reaction pH | (R)-DMA Formed (%) |
|---|---|
| 7.5 | 16.8 |
| 8.0 | 30.8 |
| 8.5 | 40.0 |
| 9.0 | 41.6 |
| 9.5 | 36.1 |

EXAMPLE 6

30 ml overnight preculture of the *Arthrobacter* species KNK168 strain was inoculated to a 1.5 liter J medium (5 g/L KH$_2$PO$_4$, 5 g/L K$_2$HPO$_4$, 1 g/L NaCl, 1 g/L MgSO$_4$.7H$_2$O, 0.005 g/L FeSO$_4$.7H$_2$O, 0.001 g/L ZnSO$_4$.7H$_2$O, 0.001 g/L MnCl$_2$.4H$_2$O, 0.0005 g/L CuSO$_4$.5H$_2$O (pH 7.5), 40 g/L glycerol, 3 g/L yeast extract powder, 20 g/L PRO-EX (BANSYU CHOMIRYO CO., LTD.), a pH being adjusted to 7.5) in a 2 liter-mini jar, and the bacterium was cultured at 30° C. at 0.5 vvm at 450 rpm for 43 hours while keeping and adjusting the culture to a pH of 7.5 with 10% sodium hydroxide. Incidentally, after 14 hours from the start of culturing, (RS)-1-methylpropylamine filtered by a microorganisms exclusion filter was added so as to have a final concentration 4 g/L. The final cell concentration (OD$_{610}$) was about 29 at the end of the culturing, and the transaminase activity was 0.3 units per the culture medium at that time. Incidentally, the unit of enzymatic activity means the intensity of the enzymatic activity which converts a 1 μM substrate of 1-(3,4-dimethoxyphenyl)-2-propanone to (R)-1-(3,4-dimethoxyphenyl)-2-aminopropane at 30° C. in 1 minute.

The cells harvested from the 1.5 liter culture were suspended in a reaction mixture (pH 8.5) containing 45 g 1-(3,4-dimethoxyphenyl)-2-propanone, 28.3 g (R)-1-phenylethylamine, and 65.0 g oleic acid. The mixture was reacted at 30° C. for 39 hours. As a result, 81.6% of the substrate was converted to (R)-1-(3,4-dimethoxyphenyl)-2-aminopropane. After the pH of the reaction mixture was adjusted to 2.0 with hydrochloric acid, the reaction mixture was extracted with toluene to separate ketones by migrating the ketones to the organic layer. After the pH of the aqueous layer was adjusted to 12 with sodium hydroxide, the reaction mixture was extracted with toluene again, and 32.9 g (R)-1-(3,4-dimethoxyphenyl)-2-aminopropane was contained in the organic layer. The separation of the desired compound from the extract was carried out by distillation. As a result, 30.3 g (R)-1-(3,4-dimethoxyphenyl)-2-aminopropane was contained in the main distillate fraction. The total yield obtained from the sequential procedures was about 68.7%, and the optical purity was about 99.6% ee (R-form).

EXAMPLE 7

The *Arthrobacter* species KNK168 strain was subjected to shaking culture in a Sakaguchi flask containing 400 ml R medium at 30° C. for 30 hours. After harvesting the cells, the cells were suspended in 40 ml 20 mM potassium phosphate buffer (pH 6.8) containing 0.1% 2-mercaptoethanol. After the cells were disrupted by ultrasonication, the precipitates were removed by centrifugation to obtain 34 ml of a cell-free extract obtained as a supernatant.

Using 10 ml of the above cell-free extract, the mixture was reacted in a 100 ml reaction mixture comprising 0.1 M Tris-hydrochloric acid buffer (pH 8.5) containing 0.5 g 1-(3,4-dimethoxyphenyl)-2-propanone and 0.34 g (R)-1-phenylethylamine at 30° C. for 24 hours. As a result, 0.36 g (R)-(3,4-dimethoxyphenyl)-2-aminopropane was formed.

EXAMPLE 8

The *Arthrobacter* species KNK168 strain was cultured in the same manner as in Example 7, and the cells were separated from 1 ml culture. The cells were suspended in a 1 ml reaction mixture containing 0.1 M Tris-hydrochloric acid buffer (pH 8.5), 40 mg racemic 1-(3,4-dimethoxyphenyl)-2-aminopropane, 20 mg pyruvic acid, and 2% sodium dodecyl sulfate. The mixture was reacted at 30° C. for 48 hours with stirring. As a result of the analysis of the mixture after the reaction, 20.5 mg 1-(3,4-dimethoxyphenyl)-2-aminopropane remained, and its optical purity was 96% ee (S-form).

EXAMPLE 9

The *Arthrobacter* species KNK168 strain was cultured in the 3.5 liter J medium at 30° C. for 43 hours using a 5 liter mini-jar in the same manner as in Example 6. The cells were harvested by centrifugation, and the harvested cells were suspended in 1 liter 20 mM potassium phosphate buffer (pH 6.8) containing 0.01% 2-mercaptoethanol. The cells were disrupted by Dynomill [(Registered Trade Mark), Switzerland], and 810 ml supernatant was separated by centrifugation. Protamine sulfate was added to this supernatant so as to give a concentration 50 mg/ml, and nucleic acids were removed. Ammonium sulfate was added thereto so as to have a concentration 30% to saturation, and the precipitated protein was removed. Thereafter, ammonium sulfate was added again so as to have a concentration 60% to saturation, and the precipitated protein was separated. This protein was dissolved in the above-mentioned buffer, and it was dialyzed against the same buffer. The composition of the buffer was adjusted to 20% (v/v) glycerol, 0.3 M NaCl, and 20 μM pyridoxal phosphate, and thereafter applied to a DEAE-Sepharose, Fast-Flow (Pharmacia) column (φ 4.4 cm×20 cm) equilibrated with this solution, which was eluted with an NaCl linear concentration gradient 0.3 to 0.5 M.

After this active fraction was collected and dialyzed, ammonium sulfate was added thereto so as to give a concentration 0.2 M. Thereafter, the active fraction was applied to Phenyl-Sepharose (Pharmacia) column (φ 2.2 cm×17 cm) equilibrated with the above buffer containing 0.2 M ammonium sulfate in place of 0.3 M NaCl, which was eluted with an ammonium sulfate linear concentration gradient 0.2 to 0 M. After the concentration of the ammonium sulfate in the active fraction was adjusted to 0.6 M, the active fraction was applied to Butyl-Sepharose (Pharmacia) column (φ 2.2 cm×17 cm) equilibrated with the above buffer containing 0.2 M ammonium sulfate in place of 0.3 M NaCl, which was eluted with an ammonium sulfate linear concentration gradient 0.6 to 0.2 M. The active fraction was collected and concentrated by ultrafiltration. Thereafter, the concentrated fraction was subjected to electrophoresis with SDS-polyacrylamide gel, and as a result, substantially a single band was formed at the position corresponding to a molecular weight of about 37,000.

EXAMPLE 10

The amino acid sequence in the amino terminal of the purified enzyme proteins obtained in Example 9 was analyzed by Gas-Phase Protein Sequencer (470A, Applied Biosystems, Inc.). As a result, it was found that each of the above enzyme proteins had two kinds of amino acid sequences as shown in SEQ ID NO:8 and SEQ ID NO:9 in Sequence Listing. The enzyme protein having the amino acid sequence as shown in SEQ ID NO:8 at the amino terminal was present in a trace amount as compared with the enzyme protein having the amino acid sequence as shown in SEQ ID NO:9 at the amino terminal. By the comparison of the both sequences, it was deduced from the processing in the neighborhood of the amino terminal that the transaminase having the amino acid sequence as shown in SEQ ID NO:9 at the amino terminal was formed from that of SEQ ID NO:8.

8 μg TPCK trypsin was added to 100 μg purified transaminase [50 mM Tris-hydrochloric acid buffer (pH 8.0), 10% glycerol, 0.005% mercaptoethanol, and 10 μM pyridoxal phosphate], and the mixture was treated at 37° C. for 24 hours. The resulting digested product was separated and purified by HPLC (manufactured by YMC Co., Ltd., YMC-Pack PROTEIN-RP column; flow rate 1 mL/minute; eluent A: 0.1% trifluoroacetate; eluent B: 0.1% trifluoroacetate and 80% acetonitrile; elution conditions: A sample is applied to the column equilibrated with a mixed solution of 90% eluent A and 10% eluent B, and the proportion of eluent B is increased to 100% in 90 minutes). The amino acid sequencing was carried out for each peptide fragment by the method described above. As a result, partial amino acid sequences of SEQ ID NO:10 and SEQ ID NO:11 were obtained.

EXAMPLE 11

Using the purified enzyme protein obtained in Example 9, reactivities to various amino compounds when using pyruvic acid as an amino acceptor were evaluated. A 150 μl solution of the purified enzyme protein solution diluted ten-folds was added to a 150 μl substrate solution [0.1 M potassium phosphate buffer (pH 8.3), 40 mM pyruvic acid, 0.1 mM pyridoxal phosphate, and 40 mM various amino compounds]. The components were reacted at 30° C. for 1 hour. The reaction tube was transferred into boiling water to stop the reaction, and thereafter, a part of the reaction mixture was diluted five-folds. Ten μl 0.1 M boric acid buffer (pH 8.0) and a 20 μl ethanol solution of 80 mM 4-fluoro-7-nitro-2,1,3-benzoxadiazole (NBD-F) were added to the 10 μl above-mentioned diluted reaction mixture. The resulting mixture was reacted at 60° C. for 1 minute, and thereafter, the resulting mixture was ice-cooled, and 460 μl 5 mM HCl was added thereto. This reaction mixture was analyzed by high-performance liquid chromatography using a fine pack C18-5 column (manufactured by Nippon Bunko) I and using 0.1 M potassium phosphate buffer (pH 6.5) and $CH_3CN$ (90:10) as an eluent to detect formation of NBD-Alanine with an excitation wavelength of 470 nm and a detection wave of 530 mm. The results thereof are shown in Table 8 in terms of relative activity in the case of using (R)-1-phenylethylalanine as a substrate.

It is apparent from the Table 8 that (S)-2-phenylglycinol, 3-aminophenylbutane, and the like, showed favorable reactivities.

TABLE 8

| Compound | Relative Activity (%) |
| --- | --- |
| (R)-1-Phenylethylamine | 100 |
| (R)-1-(3,4-Dimethoxyphenyl)-2-aminopropane | 30 |
| 1-Methylheptylamine | 47 |
| 2-Methylhexylamine | 37 |
| 1-Methylpropylamine | 1.2 |
| Benzylamine | 0.8 |
| (S)-2-Phenylglycinol | 180 |
| 3-Aminophenylbutane | 84 |
| L-Phenylalaninol | 0.8 |
| (S)-1-Phenylethylamine | 0 |
| (R)-2-Phenylglycinol | 0 |

EXAMPLE 12

Using the purified enzyme protein obtained in Example 9, reactivities to various carbonyl compounds using (R)-1-phenylethylamine as an amino group donor were evaluated. A 50 µl solution of the purified enzyme protein was added to 200 µl substrate solution [0.1 M Tris-HCl buffer (pH 8.5), 25 mM (R)-1-phenylethylamine, 0.1 mM pyridoxal phosphate, and 25 mM various carbonyl compounds], and the mixture was reacted at 30° C. for 1 to 3 hours in tube. The reaction tube was transferred into boiling water to stop the reaction, and thereafter, the reaction mixture was diluted five-folds with methanol. This diluted solution was analyzed by high-performance liquid chromatography using a fine pack C18-5 column and using methanol-water (20:80) as an eluent to quantitate acetophenone formed by the reaction. The results thereof are shown in Table 9 in terms of relative activity in the case of using pyruvic acid as a substrate. It is apparent from the Table 9 that oxalacetic acid, phenoxy-2-propanone, and the like also showed favorable reactivities.

TABLE 9

| Compound | Relative Activity (%) |
| --- | --- |
| Pyruvic acid | 100 |
| Oxalacetic acid | 87 |
| Glyoxylic acid | 4 |
| 2-Ketobutyric acid | 7 |
| Ethyl pyruvate | 27 |
| Ethyl acetoacetate | 4 |
| 2-Decane | 3 |
| 4-Methoxyphenyl acetone | 14 |
| 1-(3,4-Dimethoxyphenyl)-2-propanone | 7 |
| Benzyl acetone | 3 |
| 4-(4-Methoxyphenyl)-2-butanone | 7 |
| 1-Phenyl-2-butanone | 1 |
| Phenyl acetaldehyde | 13 |
| Ethyl benzoyl acetate | 2 |
| Phenoxy-2-propanone | 83 |
| Diacetyl | 10 |
| 1-Methoxy-2-propanone | 16 |
| 1-Tetralone | 1 |
| 2-Acetylpyridine | 19 |
| 3-Acetylpyridine | 8 |
| 4-Acetylpyridine | 27 |
| 3-Acetoxypyridine | 1 |
| 2-Acetylpyrazine | 17 |
| 2-Acetylfuran | 2 |
| 2-Acetylthiophene | 1 |
| 2-Acetylthiazole | 10 |

EXAMPLE 13

The *Arthrobacter* species KNK168 strain was cultured in the same manner as in Example 7, and the cells were separated from 1 ml culture. The cells were suspended in 1 ml reaction mixture containing 0.1 M Tris-hydrochloric acid buffer (pH 8.5), 100 mM (R)-1-phenylethylamine, 100 mM methoxy-2-propanone, and 0.1% sodium dodecyl sulfate. The mixture was reacted at 30° C. for 20 hours with stirring. As a result of the analysis of the reaction mixture, it was found that methoxy-2-propanone, the substrate, almost disappeared and was converted to 2-amino-1-methoxypropane, and its optical purity was 99.4% ee [(R)-form].

EXAMPLE 14

The *Arthrobacter* species KNK168 strain was cultured in the same manner as in Example 13, and the cells were separated from 1 ml culture. The cells were suspended in 1 ml reaction mixture containing 0.1 M Tris-hydrochloric acid buffer (pH 8.5), 50 mg racemic 2-amino-1-methoxypropane, 37.5 mg pyruvic acid, and 0.1% sodium dodecyl sulfate. The mixture was reacted at 30° C. for 24 hours with stirring. As a result of the analysis after the reaction, 23.4 mg 2-amino-1-methoxypropane remained, and its optical purity was 95% ee [(S)-form].

EXAMPLE 15

The same reaction as in Example 14 was carried out using 200 mM racemic 2-amino-1-methoxypropane, and 150 mM n-butylaldehyde or propionaldehyde, and the mixture was reacted at 30° C. for 20 hours. As a result of the analysis thereof, the (S)-form of 2-amino-1-methoxypropane was concentrated, and the ratio of the (S)-form was 76% in a case of using n-butylaldehyde, and 58% in a case of using propionaldehyde.

EXAMPLE 16

The influence of pH on the activity was evaluated by using the purified enzyme protein obtained in Example 9. An 0.1 ml enzyme protein solution which was diluted suitably beforehand was added to 0.9 ml solution containing 20 µmol 1-(3,4-dimethoxyphenyl)-2-propanone, 20 µmol (R)-1-phenylethylamine, and 1 µmol pyridoxal phosphate, of which the pH was adjusted using the buffer described as follows. The mixture was reacted at 30° C. for 1 hour. The used buffers were an acetic acid buffer (abbreviated as $CH_3COONa$; pH 4 to 6), a potassium phosphate buffer (KPB; pH 5 to 8), and a Tris-hydrochloric acid buffer (Tris-HCl; pH 7 to 10), all of these buffers having final concentrations 0.1 M. The formed (R)-DMA in the reaction mixture after the reaction was quantitated by high-performance liquid chromatography. The relative activity at each pH, relative to the activity at pH 8.5 as being 100%, is shown in FIG. 1. It has been found that the optimum pH of this enzyme protein is in the neighborhood of pH 8.5 (pH 7.5 to 9.0).

EXAMPLE 17

The influence of the pH on the stability of the enzyme was evaluated by using the purified enzyme protein obtained in Example 9. After the pH of the enzyme protein solution was adjusted by HCl or NaOH to each pH, the reaction mixture was incubated at 20° C. for 23 hours. Thereafter, in the same manner as in Example 16, the mixture was reacted at pH 8.5, and the formed (R)-DMA was quantitated. The results in which the relative activities of the treated samples at each pH, relative to the activity of the untreated enzyme protein solution as being 100%, are shown in FIG. 2. It has been found that this enzyme protein is most stable at a pH in the neighborhood of 7.

EXAMPLE 18

Chromosomal DNA was prepared from *Arthrobacter* species KNK168 strain. The *Arthrobacter* species KNK168 strain was inoculated to 30 ml the following medium contained in a 500 ml-Sakaguchi flask. The medium was subjected to shaking culture at 30° C. for 2 days, and thereafter the culture medium was centrifuged to harvest the cells. The cells were suspended in 10 mM Tris-hydrochloric acid buffer at pH 8.0, 1 mM EDTA (abbreviated as TE), and thereafter chromosomal DNA was prepared in accordance with a method in *Current Protocol in Molecular Biology* (F. Ausubel et al., Willy Interscience). Here, the SDS treatment concentration used in this method was changed from 0.5% to 2%. An about 6.5 mg chromosomal DNA was obtained from 15 ml culture.

| Medium Composition | |
|---|---|
| Glycerol | 2% by weight |
| Yeast Extract | 0.8% by weight |
| $KH_2PO_4$ | 0.5% by weight |
| $K_2HPO_4$ | 0.5% by weight |
| B Solution | 10% by volume |
| Distilled Water | Balance |
| | pH 7.5 |
| Composition of B Solution | |
| $MgSO_4.7H_2O$ | 80 g |
| $ZnSO_4.7H_2O$ | 6 g |
| $FeSO_4.7H_2O$ | 9 g |
| $CuSO_4.5H_2O$ | 0.5 g |
| $MnSO_4.4H_2O$ | 1 g |
| NaCl | 10 g |
| | /10 L |

EXAMPLE 19

A plasmid library was prepared by a method by T. Maniatis et al. (*Molecular Cloning*, Cold Spring Harbor Press). The chromosomal DNA was partially digested with a restriction enzyme Sau3AI, and electrophoresed on agarose gel. A gel containing an about 6 to 12 kb DNA was cut out, and purified with SUPREC™-01 (manufactured by Takara Shuzo Co., Ltd.). pUC19 was digested with a restriction enzyme BamHI, and the digested fragments were dephosphorylated with an alkaline phosphatase. The pUC19 thus treated was ligated with the partially digested chromosomal DNA using DNA Ligation kit ver.2 (manufactured by Takara Shuzo Co., Ltd.). *Escherichia coli* JM109 was transformed with the ligated product and plated on L medium containing 100 μg/ml ampicillin, 40 μg/ml X-GAL (5-bromo-4-chloro-3-indolyl-β-D-galactopyranoside), 100 μM IPTG (isopropyl-β-D-thiogalactopyranoside). The pUC19 incorporated with the chromosomal DNA formed white colonies, while the pUC19 without incorporation of the chromosomal DNA formed blue colonies, so that they can be easily distinguished.

EXAMPLE 20

Oligonucleotides as shown in SEQ ID NO:12 (AT-1) and SEQ ID NO:13 (AT-3) were synthesized based on the amino acid sequences as shown in SEQ ID NO:8, SEQ ID NO:9 and SEQ ID NO:10 in Sequence Listing obtained in Example 10.

PCR reaction was carried out using AT-1 and AT-3 as primer DNAs and chromosomal DNA of *Arthrobacter* species KNK168 strain as a template. TaKaRa Ex Taq (manufactured by Takara Shuzo Co., Ltd.) was used as a DNA polymerase, and the reaction composition was in accordance with the protocol thereof. The conditions for the reaction temperatures were as follows.
1) 94° C., 2 minutes
2) 94° C., 1 minute
3) 44° C., 1 minute
4) 68° C., 2 minutes
5) 68° C., 5 minutes
2) to 4) being repeated for 30 cycles.

After the termination of reaction, the resulting product was evaluated by 6% polyacrylamide gel electrophoresis, and as a result, there was confirmed the presence of an about 450 bp of amplified DNA fragment in a small amount.

A gel containing an about 450 bp DNA fragment was cut out, and broken into pieces by a glass rod. Thereafter, the fragment was extracted with TE buffer and purified. This fragment was cloned into pT7Blue Vector using Regular pT7Blue T-vector kit (manufactured by Novagen), to give pAT1. The nucleotide sequence regarding the insert in pAT1 was determined by ABI373A DNA Sequencer (manufactured by Perkin-Elmer K.K.) using DNA sequencing kit (Dye Terminator Cycle Sequencing Ready Reaction) manufactured by K.K. Perkin-Elmer Japan. As a result, there has been elucidated the presence of the nucleotide sequences corresponding to the amino acid sequences as shown in SEQ ID NOs:8–11 obtained in Example 10. The nucleotide sequence of the DNA insert (about 450 bp) of pAT1 was shown in SEQ ID NO:26 in Sequence Listing.

EXAMPLE 21

A gel containing an about 450 bp DNA fragment resulting from digesting pAT1 with BamHI, and separating the resulting DNA fragment by agarose gel electrophoresis was cut out. The DNA fragment mentioned above was purified using SUPUREC™-01 (manufactured by Takara Shuzo Co., Ltd.). This DNA fragment was radiolabeled with [α-$^{32}$P]dCTP using Random Primer DNA Labeling kit Ver.2 (manufactured by Takara Shuzo Co., Ltd.) to be used as a probe. The plasmid library prepared in Example 19 was screened by carrying out colony hybridization with the probe described above. The colony hybridization was carried out in accordance with the method of T. Maniatis et al. (*Molecular Cloning*, Cold Spring Harbor Press). A plasmid library comprising about 2000 clones was cloned, and as a result, two positive clones JM109 (pAT11) and JM109 (pAT17) were obtained. The pAT11 was inserted with an about 8 kb chromosomal DNA fragment, and the pAT17 was inserted with an about 10.5 kb chromosomal DNA fragment.

Figure 3:
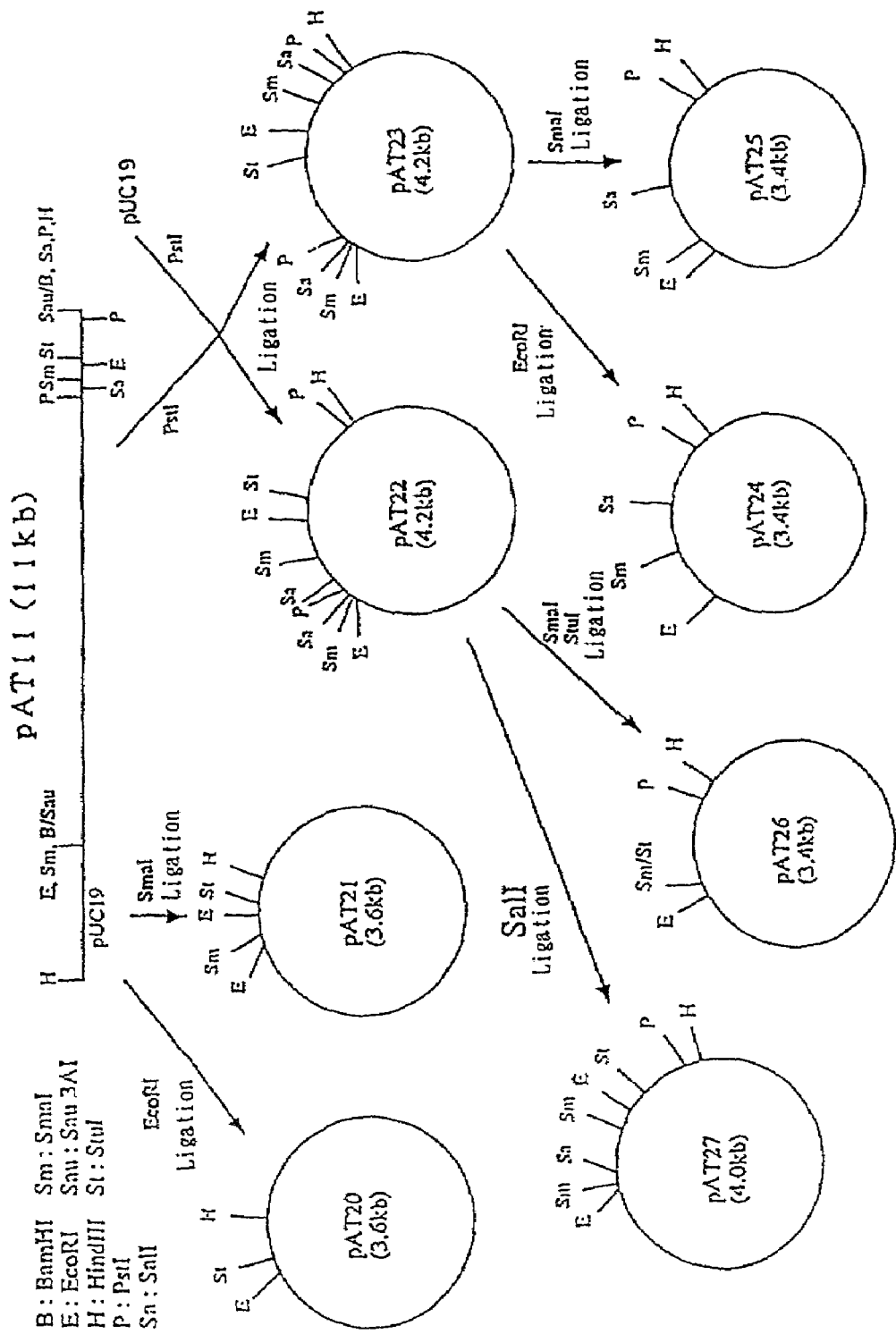
FIG. 3 is a view showing methods for preparing plasmids carrying the present enzyme gene, and simple restriction enzyme maps.

The pAT11 was digested with various restriction enzymes to prepare restriction enzyme maps (FIG. 3). It was suggested from the results of comparison of the restriction enzyme map of the nucleotide sequence (SEQ ID NO:26) of the DNA insert of pAT1 with that of pAT11, and the size of ORF (about 1 kb) deduced from molecular weight (MW 37,000) of transaminase that an entire length of the gene is contained in the DNA fragment of about 1.6 kb resulting from digestion of pAT11 with PstI.

The pAT11 was digested with PstI, and electrophoresed on agarose gel. A gel containing a 1.6 kb DNA fragment was cut out. Thereafter, the fragment was extracted and purified with SUPREC™-01 (manufactured by Takara Shuzo Co., Ltd.). pUC19 was digested with PstI, and mixed with the 1.6 kb DNA fragment, and the digested fragments were ligated using DNA Ligation kit Ver.2 (manufactured by Takara Shuzo Co., Ltd.). *Escherichia coli* JM109 was transformed with the ligated DNA to give a transformant. A plasmid DNA was prepared from the resulting transformant. This plasmid DNA was digested with various restriction enzymes including PstI, and the digested DNA fragments were analyzed, and as a result, it was found that pAT22 and pAT23 having different insertion orientations were obtained. Simple restriction enzyme maps for pAT22 and pAT23 were shown in FIG. 3. The bacterial cell harboring the pAT22 was named *E. coli* JM109 (pAT22), and deposited with an accession number FERM BP-5902 with National Institute of Bioscience and Human-Technology, Agency of Industrial Science and Technology [address: 1-3, Higashi 1-chome, Tsukuba-shi, Ibaraki-ken, Japan (zip code: 305-0046)], since Apr. 8, 1997 (date of original deposit).

In order to determine the nucleotide sequence of the 1.6 kb PstI fragment, various plasmid DNAs were prepared. The pAT11 was digested with EcoRI and SmaI, respectively, and ligated using DNA Ligation kit Ver.2 (manufactured by Takara Shuzo Co., Ltd.). *Escherichia coli* JM109 was transformed with the ligated DNA to give a transformant. A plasmid DNA was prepared from the resulting transformant, and the plasmid DNA was digested with various restriction enzymes. As a result, it was found that there were obtained plasmids pAT20 and pAT21 in which a region from EcoRI or SmaI site in the neighborhood of StuI within the DNA insert to EcoRI or SmaI site of the vector was deleted, respectively. The pAT22 was digested with SmaI and StuI, and the digested fragments were ligated using DNA Ligation kit Ver.2 (manufactured by Takara Shuzo Co., Ltd.). *Escherichia coli* JM109 was transformed with the ligated DNA to give a transformant. A plasmid DNA was prepared from the resulting transformant, and the plasmid DNA was digested with various restriction enzymes. The digested DNA fragments were analyzed, and as a result, it was found that there was obtained plasmid pAT26 in which an about 350 bp SmaI-StuI fragment was deleted. The pAT23 was digested with EcoRI, and the digested fragments were ligated. *Escherichia coil* JM109 was transformed with the ligated product.

A plasmid DNA was prepared from a transformant and analyzed with various restriction enzymes. As a result, it was found that there was obtained a plasmid pAT24 in which an about 900 bp region from EcoRI site of the vector to EcoRI site within the DNA insert was deleted. The pAT23 was digested with SmaI, and the digested fragments were ligated in the same manner. *Escherichia coli* JM109 was transformed with the ligated product. A plasmid DNA was prepared from the resulting transformant, and analyzed with various restriction enzymes. As a result, it was found that there was obtained a plasmid pAT25 in which an about 1,100 bp region from SmaI of the vector to SmaI site within the DNA insert was deleted. The pAT22 was digested with SalI, and the digested fragments were ligated in the same manner. *Escherichia coli* JM109 was transformed with the ligated product. A plasmid DNA was prepared from the resulting transformant, and analyzed with various restriction enzymes. As a result, it was found that there was obtained a plasmid pAT27 in which an about 200 bp region from SalI of the vector to SalI site within the DNA insert was deleted.

Preparation methods and simple restriction enzyme maps for each plasmids pAT20 to pAT327 were shown in FIG. 3.

The nucleotide sequences were determined by the method shown in Example 20 using these plasmid DNAs as templates, and M13-47 (manufactured by Takara Shuzo Co., Ltd.) and RV-M (manufactured by Takara Shuzo Co., Ltd.) as primer DNAs. In addition, on the basis of the nucleotide sequences sequentially determined in the manner described above, the oligonucleotides of SEQ ID NOS:14–20 were synthesized, and the nucleotide sequences were further determined using the oligonucleotides of SEQ ID NOS: 14–20 (AT-6 to 9, 11, 12, 18) in Sequence Listing as primers. The nucleotide sequence of the 1.6 kb PstI fragment thus determined was shown in SEQ ID NO:21 in Sequence Listing.

The amino acid sequence corresponding to the nucleotide sequence of SEQ ID NO:21 was compared with the amino acid sequences near the amino terminal determined in Example 10 (SEQ ID NOS:8–9), and as a result, it was found that the translation of the gene encoding transaminase was initiated at GTG from 386th to 388th in the nucleotide sequence of SEQ ID NO:21. In addition, in the majority of the transaminase prepared from *Arthrobacter* species KNK168, 6 amino acids from amino terminal methionine were cleaved and removed, and that the amino terminal was found to be threonine. The amino acid sequence corresponding to the region encoding a protein and the nucleotide sequence are shown in SEQ ID NOS:1–4 and SEQ ID NOS:5–7 in Sequence Listing, respectively.

EXAMPLE 22

In order to produce transaminase in *Escherichia coli*, an expression vector for the above gene was constructed. pUCNT (WO/03613) having a promoter for lactose operon was used as an expression vector.

PCR method was carried out to introduce a restriction enzyme site necessary for inserting the transaminase gene to the expression vector. There were synthesized oligonucleotides of SEQ ID NOS:22–24 (AT-13 to 15) as amino terminal primer DNAs, and oligonucleotides of SEQ ID NO:25 (AT-16) as a carboxyl terminal primer DNA. AT-13 was synthesized for the purpose of changing a translational initiation codon GTG to ATG, and AT-14 was synthesized for the purpose of changing the fifth Asp codon, GAT to ATG, as a translational initiation codon. In addition, AT-15 was prepared in order to use the translational initiation codon GTG as it is.

PCR was respectively carried out using each of the carboxyl terminal primer DNA and the three kinds of the amino terminal primer DNAs. PCR was carried out under the following temperature conditions using TaKaRa Ex Taq.

1) 94° C. for 2 minutes
2) 94° C. for 1 minute
3) 50° C. for 1 minute
4) 68° C. for 2 minutes
5) 68° C. for 5 minutes
2) to 4) being repeated for 30 cycles.

There was found amplification of an about 1 kb DNA fragment. A DNA fragment amplified by PCR using AT-13 and AT-16 as primer DNAs, and a DNA fragment resulting from amplified by PCR using AT-14 and AT-16 as primer DNAs were digested with NdeI and BamHI. The digested fragments were separated by 0.8% agarose gel electrophoresis. The gel containing a DNA fragment was cut out, and the DNA fragment was extracted and purified with SUPREC™-01 (manufactured by Takara Shuzo Co., Ltd.). These DNA fragments were digested with NdeI and BamHI and electrophoresed on agarose gel. pUCNT obtained by cutting out from the gel, and extracting and purifying the fragment with SUPREC™-01 (manufactured by Takara Shuzo Co., Ltd.) was ligated using DNA Ligation kit Ver.2 (manufactured by Takara Shuzo Co., Ltd.). *Escherichia coli* JM109 was transformed with each of the ligated genes. A plasmid DNA was prepared from the resulting transformant, and analyzed. As a result, it was found that there were obtained expression plasmids pAT28, pAT29 in which each transaminase gene was inserted, respectively.

A DNA fragment amplified by PCR using AT-15 and AT-16 as primer DNAs was digested with PmaCI and BamHI, and the DNA fragment was separated by 0.8% agarose gel electrophoresis. The gel containing the DNA fragment was cut out, and the fragment was extracted and purified with SUPREC™-01 (manufactured by Takara Shuzo Co., Ltd.). The resulting pUCNT was digested with NdeI, and the cleavage site was blunted with DNA Blunting kit (manufactured by Takara Shuzo Co., Ltd.), and thereafter digested with BamHI. Thereafter, the DNA fragment was separated by 0.8% agarose gel electrophoresis. The gel containing the DNA fragment was cut out, and the fragment was extracted and purified with SUPREC™-01 (manufactured by Takara Shuzo Co., Ltd.). The DNA fragment prepared in the manner described above was ligated with a vector. *Escherichia coli* JM109 was transformed with the ligated product. A plasmid DNA was prepared from the resulting transformant, and analyzed. As a result, it was found that there was obtained expression plasmid pAT30 in which a transaminase gene was inserted.

EXAMPLE 23

Expression (production) of transaminase was carried out using *Escherichia coli* JM109 harboring pAT28 [hereinafter simply referred to as *E. coli* JM109 (pAT28)], *E. coli* JM109 (pAT29), or *E. coli* JM109 (pAT30), each of which was prepared in Example 22. As a control, *E. coli* JM109 (pUCNT) was used. In addition, the supernatant of centrifuge after disruption of the *Arthrobacter* species KNK168 cells described in Example 9 by Dynomill was used as a control.

Each strain was inoculated to a 10 ml L medium containing 100 µg/ml IPTG, 100 µg/ml ampicillin in a test tube (diameter 22 mm, length 220 mm), and thereafter subjected to shaking culture at 37° C. overnight. 1.5 ml the resulting culture was centrifuged (15,000 rpm, 5 minutes, 4° C.) to harvest the cells. The cells were suspended by adding 1 ml extract buffer cooled to 4° C., comprising 20 mM phosphate buffer at pH 6.8, 20 µM pyridoxal phosphate, 0.01% 2-mercaptoethanol. This suspension was ultrasonically disrupted (manufactured by Tommy Seiko K.K.; Handy Sonic, Model UR-20P, twice for 90 sec. at power max.) on ice, and then centrifuged at 15,000 rpm and 4° C. for 10 minutes. The cell residue was removed, and the supernatant was used as crude enzyme protein solution.

The transaminase activity was measured as follows. A 0.2 ml enzyme protein solution was added to 0.8 ml substrate solution comprising 25 mM (R)-phenylethylamine, 25 mM pyruvic acid, 0.1 mM pyridoxal phosphate, 100 mM Tris-hydrochloric acid buffer at pH 8.5, and the mixture was reacted at 30° C. for 1 hour. The resulting mixture was heated for 3 minutes in boiling water to stop the reaction.

The enzyme activity was obtained by analyzing the reaction product, acetophenone, by HPLC. The analysis conditions are as shown below. Incidentally, the amount of transaminase is a value deduced from specific activity of purified transaminase.

| HPLC Column: | Manufactured by Nippon Bunko; "Finepac SIL C18-5" |
|---|---|
| Developing Solvent: | Acetonitrile/water = 25/75 |
| Flow Rate: | 1 ml/min |
| Detection: | at 210 nm |

Acetophenone was detected at about 24 minutes. The results are shown below.

| Strain | Transaminase (mg/L) |
|---|---|
| *E. coli* JM109 (pAT28) | 81 |
| *E. coli* JM109 (pAT29) | 66 |
| *E. coli* JM109 (pAT30) | 3.4 |
| *Arthrobacter* sp. KNK168 | 19 |

EXAMPLE 24

The *Arthrobacter* species KNK168 strain was subjected to shaking culture by using (RS)-1-methylpropylamine as an inducer for enzyme in the same manner as Example 6. The cells harvested from 1 liter culture were suspended in 1 liter of 0.1 M Tris-hydrochloric acid buffer. Thereto were added a mixture of 30 g 1-(3-trifluoromethylphenyl)-2-propanone, 18 g (R)-1-phenylethylamine, and 44 g oleic acid (pH 8.5), and the resulting mixture was reacted at 30° C. for 40 hours. After reaction, the extraction and distillation were carried out in the same manner as in Example 6, to give 19.5 g (R)-1-(3-trifluoromethylphenyl)-2-aminopropane. The optical purity was 100% ee, and the yield was 65%.

INDUSTRIAL APPLICABILITY

According to the present invention, it is made possible to easily prepare at a high yield the optically active amino compounds and the like having an aryl group and the like at their 1-position, which have been conventionally difficult to prepare. In addition, the polypeptide of the present invention has a stereoselective transaminase activity, and can be suitably used for the production method of the present invention. In addition, the DNA of the present invention encodes the polypeptide of the present invention.

What is claimed is:

1. An isolated or purified DNA encoding an entire or partial amino acid sequence of any one of SEQ ID NOS:1–4, wherein the partial amino acid sequence of any one of SEQ ID NOS:1–4 has a stereoselective transaminase activity.

2. An isolated or purified DNA comprising an entire or partial nucleotide sequence of any one of SEQ ID NOS:5–7, wherein the partial nucleotide sequence of any one of SEQ ID NOS:5–7 encodes a polypeptide having stereoselective transaminase activity.

3. A recombinant DNA comprising the DNA according to claim 1 or 2.

4. The recombinant DNA according to claim 3, wherein the recombinant DNA is capable of expressing a polypeptide encoded thereby in microorganisms, animals, animal cells, plants or plant cells.

5. An expression vector resulting from insertion of the recombinant DNA according to claim 3 for transforming microorganisms, animal cells or plant cells as host cells.

6. An isolated transformed cell obtainable by transforming a host cell with the expression vector according to claim 5.

7. The transformed cell according to claim 6, wherein the host cell is *Eseherichia coli*.

8. A method for preparing a polypeptide having stereoselective transaminase activity, comprising
   culturing the transformant according to claim 6, and
   collecting a polypeptide having stereoselective transaminase activity from the culture medium used in culture or the transformant.

9. A method for preparing a polypeptide having stereoselective transaminase activity, comprising
   culturing the transformant according to claim 7, and
   collecting a polypeptide having stereoselective transaminase activity from the culture medium used in culture or the transformant.

* * * * *